Figure 1:
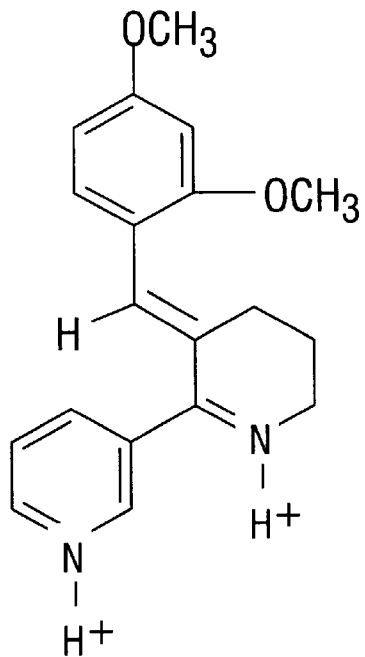

US005977144A

United States Patent [19]

Meyer et al.

[11] Patent Number: 5,977,144
[45] Date of Patent: *Nov. 2, 1999

[54] METHODS OF USE AND COMPOSITIONS FOR BENZYLIDENE- AND CINNAMYLIDENE-ANABASEINES

[75] Inventors: Edwin Meyer; William Kem; Franz van haaren; John A. Zoltewicz, all of Gainesville, Fla.; Christopher M. De Fiebre, Fort Worth, Tex.; Roger Papke; Arthur Day, both of Gainesville, Fla.

[73] Assignee: University of Florida, Gainesville, Fla.

[*] Notice: This patent issued on a continued prosecution application filed under 37 CFR 1.53(d), and is subject to the twenty year patent term provisions of 35 U.S.C. 154(a)(2).

[21] Appl. No.: 08/924,008

[22] Filed: Aug. 29, 1997

Related U.S. Application Data

[63] Continuation of application No. 08/924,008, Aug. 29, 1997, which is a continuation-in-part of application No. 08/392,763, Feb. 23, 1995, Pat. No. 5,741,802, which is a continuation-in-part of application No. 07/938,427, Aug. 31, 1992, abandoned.

[51] Int. Cl.[6] .......................... A61K 31/44; C07D 211/68
[52] U.S. Cl. .......................... 514/334; 514/318; 546/193; 546/257
[58] Field of Search ................................ 514/334, 318; 546/193, 259

[56] References Cited

U.S. PATENT DOCUMENTS

| | | | |
|---|---|---|---|
| 3,247,213 | 4/1966 | Buchel et al. | 546/193 |
| 3,265,573 | 8/1966 | Goldberg | 167/65 |
| 3,275,625 | 9/1966 | Muller et al. | 260/243 |
| 3,426,130 | 2/1969 | Riffkin et al. | 514/223.2 |
| 4,155,909 | 5/1979 | Sanders et al. | 546/193 |
| 4,195,645 | 4/1980 | Bradley et al. | 131/2 |
| 4,728,605 | 3/1988 | Fudenberg et al. | 435/29 |
| 4,965,074 | 10/1990 | Leeson et al. | 424/449 |
| 5,015,570 | 5/1991 | Scangos et al. | 435/6 |
| 5,187,169 | 2/1993 | Lippiello et al. | 514/343 |
| 5,212,188 | 5/1993 | Caldwell et al. | 514/343 |
| 5,214,060 | 5/1993 | Caldwell et al. | 514/343 |
| 5,227,385 | 7/1993 | Caldwell et al. | 514/304 |
| 5,227,391 | 7/1993 | Caldwell et al. | 514/343 |
| 5,232,932 | 8/1993 | Caldwell et al. | 514/343 |
| 5,232,933 | 8/1993 | Lippiello et al. | 514/343 |
| 5,242,916 | 9/1993 | Lippiello et al. | 514/214 |
| 5,242,934 | 9/1993 | Lippiello et al. | 514/343 |
| 5,242,935 | 9/1993 | Lippiello et al. | 514/343 |
| 5,248,690 | 9/1993 | Caldwell et al. | 514/408 |
| 5,276,043 | 1/1994 | Lippiello et al. | 514/343 |
| 5,516,785 | 5/1996 | Zoltewicz et al. | 514/334 |
| 5,602,257 | 2/1997 | Zoltewicz et al. | 546/193 |
| 5,741,802 | 4/1998 | Kem et al. | 514/334 |

FOREIGN PATENT DOCUMENTS

| | | |
|---|---|---|
| 0 435 387 A1 | 7/1991 | European Pat. Off. . |
| 0 567 251 A1 | 7/1993 | European Pat. Off. . |
| WO 92/15306 | 9/1992 | WIPO . |
| WO 94/05288 | 3/1994 | WIPO . |
| WO 95/15759 | 6/1995 | WIPO . |

OTHER PUBLICATIONS

Arendash et al., "Improved learning and memory in aged rats with chronic administration of the nicotinic receptor agonist GTS–21," *Brain Research*, 674:252–259, 1995.

Arendash et al., "Nicotine enhances the learning and memory of aged rats," *Pharm. Biochem. Behavior*, 52(3):517–523, 1995.

Arneric et al., "Neuronal nicotinic acetylcholine receptor (nAChR) diversity and therapeutic potential of selective ligands," In: *Book of Abstracts*, Issue Pt. 2, (210th ACS National Meeting, American Chemical Society, Washington, D.C., Neuroscience Research, Abbott Laboratories, Abbott Park, IL, Aug. 20–24, 1995.

Baron, "Cigarette smoking and Parkinson's disease," *Neurology*, 36:1490–1496, 1986.

Briggs et al., "Ganglionic nicotinic acetylcholine receptor activation by the novel agonist ABT–418," *Drug Dev. Res.*, 34:39–46, 1995.

Briggs et al., "Human α7 nicotinic acetylcholine receptor responses to novel ligands," *Neuropharmacology*, 34(6):583–590, 1995.

Castonguay and Hecht, "Synthesis of carbon–14 labeled 4–(methylnitrosamino)–1–(3–pyridyl)–1–butonone," *J. Labelled Compounds Radiopharmaceuticals*, 22(1):23–28, 1984.

Clarke et al., "Electrophysiological actions of nicotine on substantia nigra single units," *Br. Pharmac.*, 85:827–835, 1985.

Fujisawa et al., "Extension of Bichler Napieralski reaction," *Chemical Abstracts*, 54(8)185–188, 1960.

Gallulo et al., "Cyclization of ω–halonitriles with organolithiums," *Chemical Abstracts*, 113(1):593, Abstract 6111k, 1990.

Gallulo et al., "Cyclization of ω–halonitriles with organolithiums," *Organic Preparations and Procedures Int.*, 21(3):297–301, 1989.

Giacobini, "Cholinergic receptors in human brain: effects of aging and alzheimer disease," *Neuros. Res.*, 27:548–560, 1990.

Grant (Ed.), In: *Hackh's Chemical Dictionary*, McGraw–Hill Book Co., New York, p. 642, 1983.

Hamlet and Durst, "1–(Dialkylaminomethyl)–azetidin–2–ones. Intermediates in a highly stereoselective preparation of trans–3,4–disubstituted azetidin–2–ones," *Canadian J. Chem.*, 61(2):411–415, 1983.

(List continued on next page.)

*Primary Examiner*—Theodore J. Criares
*Attorney, Agent, or Firm*—Arnold, White & Durkee

[57] ABSTRACT

This invention relates to compositions for benzylidene- and cinnamylidene-anabaseines and methods for using these compositions for treating conditions associated with defects or malfunctioning of nicotinic subtypes brain receptors. These compositions target the alpha7 receptor subtype with little or no activation of the alpha4beta2 or other receptor subtypes.

94 Claims, 16 Drawing Sheets

OTHER PUBLICATIONS

Hodges, "Nicotine as a tool to characterize the role of the forebrain cholinergic projection system in cognition," *Biol. of Nicotine: Current Res. Issue,* Lippiello et al. (eds), Raven Press, Ltd., NY 1992.

Hu et al., "Chemical studies on tobacco smoke XXIII. Synthesis of carbon–14 labelled myosmine, nirnicotine and N'–nitrosonornicotine," *Journal of Labelled Compounds,* 10(1):79–89, 1973.

Hunter et al., "A novel nicotinic agonist facilitates induction of long–term potentiation in the rat hippocampus," *Neuroscience Ltrs.,* 168:130–134, 1994.

International Search Report dated Nov. 12, 1993.

Jones, "Effects of acute subcutaneous nicotine on attention, information processing and short–term memory in Alzheimer's disease," *Psychopharm.,* 108:485–494, 1992.

Kellar and Wonnacott, "Nicotinic cholinergic receptors in Alzheimer's disease," In: *Nicotine Psychopharmacology,* pp. 343–373, 1992.

Kem and Papke, "Actions of anabaseine and DMAB–anabaseine upon neuronal $\alpha_4\beta_2$ and PC12 cell nicotinic receptors," *Soc. Neuroscience,* 18(2)569.19, 1992.

Kem, "A study of the occurrence of anabaseine in *paranemertes* and other nemertines," *Toxicon,* 9:23–32, 1971a.

Kem, "Biochemistry of Nemertine Toxins," *Marine Pharmacognosy,* Chapter II, 37:84, 1973.

Kem et al., "Hoplonemertine Worms—a New Source of Pyridine Neurotoxins," *Experientia,* 684–686, 1976.

Kem et al., "Isolation and structure of a hoplonemertine toxin," *Toxicon,* 9:15–22, 1971b.

Kem, "Occurance of anabaseine in paranemertes and other nemertines," *Toxicon,* 9(1):23–32, 1971. (Abstract only).

Kem, "Pyridine alkaloid distribution in the hoplonemetines," *Hydrobiologia,* 156:145–151, 1988.

Kem, "Structure and Action of Nemertine Toxins, " *American Zoology,* 25:99–111, 1985.

Kem, "Worm Toxins," *Handbook of Natural Toxins,* Marcei Dekker Inc., N.Y., 3:353–360, 1988.

Leete, "Aberrant Biosynthesis of 5–Fluoroanabasine from 5–Fluoro[5,6–$^{14}$C,$^{13}$C$_2$]nicotinic Acid, Established by Means of Carbon–13 Nuclear Magnetic Resonance," *The Journal of Organic Chemistry,* 44(2):165–168, 1979.

Leete and Chedekel, "The Aberrant Formation of (–)–N–Methylanabasine From N–Methyl–Piperideinium Chloride in *Nicotiana Tabacum* and *N. Glauca,*" *Phytochemistry,* 11:2751–2756, 1972.

Martin, "Cytoprotective actions of 2,4–dimethoxybenzylidene anabaseine in differentiated PC12 cells and septal cholinergic neurons," *Drug Dev. Res.,* 31:135–141, 1994.

Marttila and Rinne, "Progression and survival in Parkinson's disease," *Acta Neurol. Scand.,* 84(136):24–28, 1991.

McGehee et al., "Nicotine enhancement of fast excitatory synaptic transmission in CNS by presynaptic receptors," *Science,* 269:1692–1695, 1995.

Meyer et al., "Effects of anabaseine–related analogs on rat brain nicotinic receptor binding and on avoidance behaviors," *Drug Dev. Res.,* 31:127–134, 1994.

Meyer et al., "Effects of nucleus basalis lesions on the muscarinic and nicotinic modulation of [$^3$H] acetylcholine release in the rate cerebral cortex," *Neurochem.,* 49:1758–1762, 1987.

Nanri et al., "GTS–21, a nicotinic agonist, protects against neocortical neuronal cell loss induced by the nucleus basalis magnocellularis lesion in rats," *Jpn. J. Pharmacol.,* 74(3):285–289, 1997.

Nanri et al., "Protective effect of GTS–21, a novel nicotinic receptor agonist, on neuronal cell death," *Jpn. J. Pharmacol.,* 71(Supp.1):171, 1996.

Newhouse et al., "The effects of nicotinic agents on human cognition: possible therapeutic applications in Alzheimer's and Parkinson's diseases," *Med. Chem. Res.,* 2:628–642, 1993.

Nomura et al., "The reaction of 5–benzylidine–2,3,4,5–tetrahyteropyridine with some nucleophiles," *Bull Chem. Society of Japan,* 57:1271, 1984.

Papke and Heinemann, "Partial agonist properties of cytosine on neuronal nicotinic receptors containing the β2 subunit," *Molecular Pharmacology,* 45:142–149, 1993.

Papke, "The kinetic properties of neuronal nicotinic receptors: genetic basis of functional diversity," *Progress in Neurobiology,* 41:509–531, 1993.

Parcell et al., The preparation of tetrahydro pyridines from Enamies and Imines, *J. of Organic Chemistry,* 28:3469, 1963.

Pathak et al., "Synthesis of [4–$^2$H$_2$]–, (4R)[4–$^2$H$_1$]–and (4S)[4–$^2$H$_1$]–4–(methylnitrosamino)–1–(3'–pyridyl)–1–butanone, C–4 deuteriated isotopomers of the procarcinogen NNK," *Tetrahedron,* 46(5):1733–1744, 1990.

Patneau et al., "Hippocampal Neurons Exhibit Cyclothiazide–sensitive Rapidly Desensitizing Responses to Kainate," *The Journal of Neuroscience,* 13(8):3496–3509, 1993.

Rinne et al., "A postmortem study of brain nicotinic receptors in Parkinson's and Alzheimer's disease," *Brain Research,* 547:167–170, 1991.

Rinne, "New strategies in the treatment of early Parkinson's disease," *Acta Neurol. Scand.,* 84(136):95–98, 1991a.

Rinne, "Nigral degeneration in Parkinson's disease in relation to clinical features," *Acta Neurol. Scand.,* 84(136):87–90, 1991b.

Sahakian et al., "The effects of nicotine on attention, information processing, and short–term memory in patients with dementia of the Alzheimer type," *Brit. J. Psychiatry,* 154:797–800, 1989.

Schröder et al., "Nicotinic cholinoceptive neurons of the frontal cortex are reduced in Alzheimer's disease," *Neurobiology of Aging,* 12:259–262, 1991.

Seeman et al., "Steric and Conformational Effects in Nicotine Chemistry," *J. Org. Chem.,* 56:3040–3048, 1981.

Seiyaku et al., "Novel heterocyclic compounds," *Chemical Abstracts,* 59(10):11447, 1963.

Shimohama et al., "Changes in nicotinic and muscarinic cholinergic receptors in Alzheimer–type dementia," *J. Neurochem.,* 46:288–293, 1986.

Sjak–Shie et al., "Cholinergic–peptide interactions in vivo: molecular to behavioral considerations," IN: *Advances in Gene Technology: Nolecular Neurobiology and neuropharmacology,* ICSU vol. 9, 1989.

Sjak–Shie et al., "Long–term actions of nicotinic receptor stimulation in nucleus basalis lesioned rats: blockage of trans–synaptic cell loss," *Clin. Therap. Aspects Alzheim. Parkinson. Dis.,* 2:471–475, 1990.

Strong and Arendash, "The effects of nucleus basalis lesions in the rate on one way passive and active avoidance, two way avoidance, and lashly III maze learning: an animal model for SDAT," IN: *Novel Approaches to the Treatment of Alzheimer's Disease,* Meyer et al. (eds.), Plenum Press, NY, 279–292, 1989.

Topliss et al., "Antihypertensive Agents. I. Non–diuretic 2H–1,2,4–Benzothiadiazine1,1–Dioxides," *J. Org. Chem.,* 16:815, 1951.

Trapani et al., "Esi ed attivita autimicrobia in vitro di derivati sostitutiti di Fenilpiperidine E Fenilpiperazine," *II Parmaco. Science,* XL:673–674, 1985.

Waters, Cognitive Enhancing Agents; Current Status in the Treatment of Alzheimer's Disease, *Le Journal Canadien Des Sciences Neurologigues,* 15:249–256, 1988.

Werner et al., "Dihydrobenzothiadiazine1,1–Dioxides and their Diuretic Properties," *Journal of the American Chemical Society,* 82(5):1161–1166, Mar. 5, 1960.

Whitehouse et al., "Alzheimer's disease and senile dementia: loss of neurons in the basal forebrain," *Science,* 215:1237–1239, 1982.

Wiley et al., "Synthesis of 4–(methylnitrosamino)–1–(3–pyridyl)–1–butanone, 4–(carbethoxynitrosamino)–1–(3–pyridyl)–1–butanone, and N'–nitrosonornicotine labelled with tritium in the pyridine ring," *J. Labelled Compounds Radiopharmaceuticals,* 25(7):707–716, 1987.

Woodruff–Pak et al., "A nicotinic agonist (GTS–21), eyeblink classical conditioning, and nicotinic receptor binding in rabbit brain," *Brain Res.,* 645:309–317, 1994.

Woodruff–Pak et al., "Eyeblink conditioning discriminates Alzheimer's patients from non–demented aged," *NeuroReport,* 1(1):45–49, 1990.

Zawai et al., "Basal forebrain cholinergic neurons in aged rat brain are more susceptible to ibotenate–induced degeneration than neurons in young adult brain," *Brain Res.,* 589:333–337, 1992.

Zoltewicz et al., "Hydrolysis of cholinergic anabaseine and N–Methylanabaseine: Influence of cosolvents on the position of the ring–chain equilibrium–compensatory changes," *Bioorganic Chem.,* 18:395–412, 1990.

Zoltewicz et al., "Long range transmission of polar effets in cholinergic 3–arylideneanabaseines. Conformations calculated by molecular modeling," *Heterocycles,* 35(1):171–180, 1993.

Zoltewicz et al., "Quantitative determination of the ring–chain hydrolysis equilibrium constant for anabaseine and related tobacco alkaloids," *J. Organic Chem.,* 54:4462–4468, 1989.

CA, G = H
2MeOCA, G=CH₃O

4MeOCA, G=CH₃O
DMAC, G = N(CH₃)₂

GTS-21

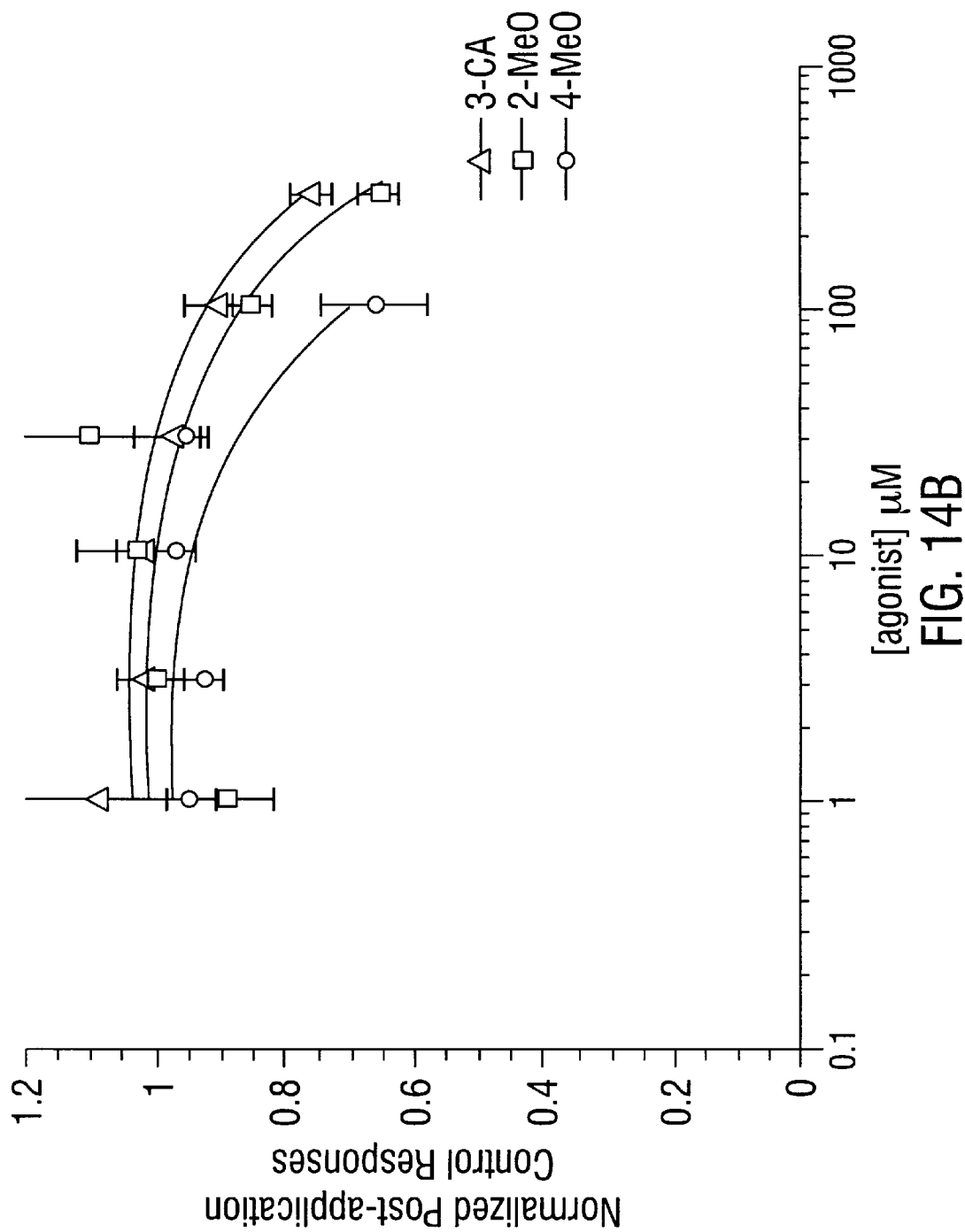

METHODS OF USE AND COMPOSITIONS FOR BENZYLIDENE- AND CINNAMYLIDENE-ANABASEINES

This is a continuation prosecution application of application Ser. No. 08/924,008, filed Aug. 29, 1997 which is a continuation-in-part of patent application Ser. No. 08/392,763 filed Feb. 23, 1995, now issued as U.S. Pat. No. 5,741,802 which is a continuation-in-part of patent application Ser. No. 07/938,427 filed Aug. 31, 1992, now abandoned.

The government owns rights in the present invention pursuant to grant numbers P01 AG01425, AG10481 and AG00176 from the United States National Institutes of Health.

1.0 BACKGROUND OF THE INVENTION

1.1 Field of the Invention

The present invention relates generally to the field of pharmacology. More particularly, it concerns novel anabaseine related compounds and methods of using these compounds for treating conditions associated with defects or malfunctioning of nicotinic subtype brain receptors.

1.2 Description of the Related Art

There are many nicotinic receptor subtypes found in brain. Nicotine is a drug that can apparently activate all of these receptor subtypes, as can the endogenous transmitter acetylcholine. Nicotine itself has both positive and negative attributes in humans, depending on the receptor subpopulation involved. The quantitatively two predominant receptor subtypes in brain are alpha7 and alpha4beta2.

A variety of molecular, biochemical and physiological studies demonstrate the presence of multiple nicotinic receptor subunits in brain and other tissues. One of the predominant nicotinic receptor subtypes in the brain contains the α7-subunit, especially in telencephalic regions such as hippocampus and neocortex. These receptors function as homo-oligomers when expressed in oocytes, where they demonstrate characteristic high affinity binding to α-bungarotoxin, high calcium-permeability, and rapid desensitization. Recent studies with selective α7 agonists suggest that these receptors are involved in memory related behaviors as well as in the maintenance of intracellular calcium-homeostasis.

The best studied selective α7 agonist is GTS-21, (E-3-[2,4-dimethoxy-benzylidene] anabaseine, also referred to as DMXB). GTS-21 enhances performance in several spatial and non-spatial memory-related paradigms in rats and rabbits. It also exerts neuroprotective activity against trophic factor deprivation in PC12 cells (Martin, et al., 1994), NMDA-receptor activation in primary neuronal cultures (Shimohama, et al., in press), and fimbrial transections in vivo (Meyer, et al. in press). Despite these behavioral and neuroprotective actions of GTS-21, however, it is only a modestly efficacious partial agonist at α7 receptors, with about 20% of the activity of ACh itself.

A fully efficacious and potent α7 agonist has been described, the 3-cinnamylidene substituted anabaseine, DMAC or E,E-3-(4-dimethylaminocinnamylidene) anabaseine.

This compound also has memory-enhancing activity in rodents, but no neuroprotective activity has not been documented. DMAC also possesses the unusual property of inducing a long term inhibition of α7 receptors following activation. While the biological significance of this inhibitory activity is not presently known, it might be expected to interfere with long term actions of the compound dependent on receptor activation such as neuroprotection.

With respect to structure activity differences between GTS-21 and DMAC, it is not known to what extent either the full agonist efficacy or the pronounced antagonist activity of the latter compound derives from its cinnamylidene-anabaseine structure or from other substituent differences.

1.2.1 Nicotine and Smoking

Nicotine is both the reinforcing and addictive agent present in tobacco smoke. In smoking addiction, all N-acetylcholine receptor subtypes are potentially activated by nicotine, including those not directly involved in producing reinforcement. Currently available replacement therapies such as nicotine-containing gums and patches, also activate all receptor subtypes. While nicotine gum and patches block some withdrawal symptoms, they also produce reinforcement. While difficult to quantify, the level of reinforcement produced by nicotine gum and patches does not appear as great as that produced by smoking, thought to be because gum and patches are not as effective as cigarettes at delivering nicotine to produce reinforcement. (de Fiebre, et al.; Collins, et al.) Hence, abuse of gum or patches does not appear to be a major problem when these products are used in smoking cessation programs. However, the rate of recidivism following the use of gum or patches remains almost as high as when no replacement therapy is provided. Although gum and patches attenuate withdrawal symptoms, their suboptimal reinforcing properties may prolong craving in recovering smokers and contributes to the high rate of smoking recidivism following their use.

Substances which inhibit the activation of nicotine receptors mediating the psychological reward/addiction properties of tobacco, administered by smoking or orally as a powder (called "snuff"), provide the ultimate therapy for acquiring a state of tobacco abstinence. This has not previously been achieved because known nicotine receptor antagonists (examples: mecamylamine, tubocurarine) are not selective for these particular nicotine receptors. Such antagonists act upon the autonomic nervous system, and at the neuromuscular synapse, causing a variety of toxic side effects, including autonomic block (causing a variety of changes including hypotension) and neuromuscular block (causing respiratory depression).

1.2.2 Ethanol and nicotine

It is well documented that smoking and drinking are positively correlated to the extent that those who smoke usually also drink and vice versa. It has been shown that ethanol can increase smoking behavior (Burton and Tiffany, 1997). Studies in rats have shown that nicotine administration can increase ethanol consumption (Blomquist, et al., 1996). Other studies have shown that cross-tolerance develops between ethanol and nicotine (Collins, et al., 1996) and that sensitivity to ethanol and nicotine are genetically correlated (de Fiebre, et al., 1992). This has suggested that ethanol and nicotine may share a common site(s) of action at one or more nicotinic receptor subtypes. Recent studies have determined that apparently the alpha7 nicotinic receptor subtype is affected by ethanol (Yu, et al., 1996).

It has been speculated that activation of brain alpha7 receptors may be implicated in the propagation of certain types of seizures (e.g., nicotine-induced seizures, (Marks et al., 1989; Miner and Collins, 1989).

1.2.3 Ischemia

Ischemia and resulting glutamate-release are a principle cause of neuronal loss in strokes, drowings and other insults to the brain. Glutamate is recognized as the principle excitotoxin responsible for much of the cell death following ischemic attack.

Nicotinic receptors have been well characterized at the neuromuscular junction as well as in electric organs of species such as *Torpedo californica*, where they form pentemetic transmembrane rings of four subunits termed α, β, δ and γ (Deneris, et al., 1991). Less is known about brain nicotinic receptors, however, with ligand-binding, electrophysiological, and molecular biological techniques demonstrating multiple receptor subtypes with new properties and functions (Martin, et al., 1994; Wright, et al., 1993). At least 6 α subunits (α2–α7, α9 in mammals; α8 in chicks), 3 β subunits (β2–β4), but no γ or δ subunits have been cloned in brain. The α7 subunit, which forms apparent functional homooligomeric receptors (Koike, et al., 1989), is the predominant nicotinic receptor subtype in brain based on quantitative binding studies (couturier, et al, 1990). Its density in hippocampus and neocortex along with the memory-enhancing actions of selective α7 nicotinic agonists such as 3-(2,4-dimethoxy-benzylidene) anabaseine (DMXB) (Pugh, et al., 1994), indicate a significant role for α7 receptors in learning and memory. In addition, these receptors are highly permeable to $Ca^{2+}$ and rapidly desensitize after activation (Alkondon, et al., 1994; Koike, et al., 1989). These channel properties suggest a modulatory function with respect to neuronal $Ca^{2+}$ homeostasis that may account for their reported involvement in synapse formation and neuronal viability (Martin, et al., 1994; Shimohama, et al., in press). Selective α7 activation has been found to protect neurons against NGF-deprivation in vitro as well as neuronal degeneration following axotomy in vivo. More recently, a mutated α7 receptor that is incapable of desensitizing has been associated with neurotoxicity in the *C. elegans* (Treinin and Chalfie, 1995).

1.2.4 Age Related Learning and Memory Loss

The loss of cholinergic neurons in Alzheimer's disease and other neuropathological disorders (e.g., pugilistic dementia; alcohol-induced dementia) is believed to underlie at least some of the memory-deficits observed in these diseases. The loss of these cholinergic neurons in animal models can be prevented using neurotrophic factors, particularly nerve growth factor ("NGF"). NGF has accordingly been developed as a potential therapy for Alzheimer's disease. However, NGF does not cross the blood brain barrier, limiting its usefulness for treating brain-disorders.

2.0 SUMMARY OF THE INVENTION

The present invention concerns two classes of compounds, novel cinnamylidene-anabaseines and benzylidene-anabaseines, that target the alpha7 receptor subtype with little or no activation of the alpha4beta2 or other subtypes. A variety of animal and human studies show that these compounds will be useful in therapies and treatments that target these receptors, including methods that reduce the side effects associated with tobacco withdrawal; have an anti-alcohol action; have anti-stroke actions, without having the side effects associated with the less specific receptor agonists; and reduce the effects of age related learning and memory impairment.

The present invention thus addresses many problems associated with defects in or malfunctioning of brain nicotinic receptor subtypes by providing compositions that target the alpha7 nicotinic receptor subtype with little or no activation of the alpha4beta2 or other receptor subtypes.

An aspect of the present invention encompasses novel compositions of matter comprising a compound of the formula:

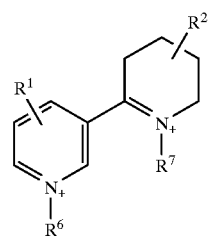

or a salt thereof, wherein $R^1$, $R^6$, and $R^7$ are hydrogen or $C_1$–$C_4$ alkyl; and $R^2$ is =CHCH=CHX, wherein X is

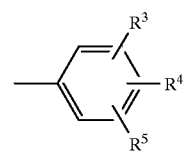

wherein $R^3$, $R^4$, and $R^5$ are selected from the group consisting of hydrogen, $C_1$–$C_4$ alkyl optionally substituted with N,N-dialkylamino having 1 to 4 carbons in each of the alkyls, $C_1$–$C_6$ alkoxy optionally substituted with N,N-dialkylamino having 1 to 4 carbons in each of the alkyls, carboalkoxy having 1 to 4 carbons in the alkoxy (such as acetoxy), amino, amido having 1 to 4 carbons in the acyl (such as acetylamino), cyano, N,N-dialkylamino having 1 to 4 carbons in each of the alkyls, halo, hydroxyl, and nitro.

In preferred embodiments $R^2$ is attached to the 3-position of the tetrahydropyridine ring. In other preferred embodiments $R^3$, which may preferably be attached to the 4- or the 2-position of the phenyl ring, is selected from the group consisting of amino, hydroxyl, chloro, cyano, dimethylamino, methyl, methoxy, pentoxy, isopentoxy, propoxy, isopropoxy, acetylamino, acetoxy, and nitro, with hydroxyl, acetylamino, acetoxy, and methoxy being particularly preferred groups. It may also be desirable for $R^1$ and $R^4$ to be hydrogen, where $R^3$ is attached to the 2-position of the phenyl ring and is an amino, hydroxyl, chloro, cyano, dimethylamino, methyl, methoxy, acetylamino, acetoxy, or nitro group, and $R^5$, which is attached to the 4-position of the phenyl ring, is methoxy or hydroxyl. Other preferred compositions include such compositions where $R^1$, $R^4$, and $R^5$ are hydrogen.

The present invention further encompasses novel cinnamylidene-anabaseines. As used herein, the term "cinnamylidene-anabaseines" refers to compounds containing both cinnamylidene and anabaseine groups. such as the cinnamylidene compounds in Table 1, Table 2, and Table 3. Thus, some preferred cinnamylidene-anabaseines encompassed by this invention include, but are not limited to, 3-(4-acetylaminocinnamylidene) anabaseine, 3-(4-hydroxycinnamylidene) anabaseine, 3-(4-methoxycinnamylidene) anabaseine, 3-(4-hydroxy-2-methoxycinnamylidene)anabaseine, 3-(2,4-dimethoxycinnamylidene) anabaseine, and 3-(4-acetoxycinnamylidene) anabaseine.

The present invention also includes the novel benzylidene-anabaseine 3-(4-isopropoxybenzylidene) anabaseine. As used herein the term "benzylidene-anabaseines" refers to compounds containing both benzylidene and anabaseine groups. Thus, benzylidene-anabaseines that may be used in practicing the methods of the present invention include, but are not limited to, 3-(2, 4-dimethoxybenzylidene) anabaseine, 3-(4-hydroxybenzylidene) anabaseine, 3-(4-methoxybenzylidene) anabaseine, 3-(4-aminobenzylidene) anabaseine, 3-(4-hydroxy-2-methoxybenzylidene) anabaseine, 3-(2-hydroxy-4-methoxybenzylidene) anabaseine, 3-(4-isopropoxybenzylidene) anabaseine, and (7'-methyl-3-(2,4-dimethoxybenzylidene)).

An important aspect of the present invention encompasses a method of moderating or preventing tobacco-withdrawal effects in a mammal, preferably a human, comprising administering to an animal in need thereof a therapeutically effective amount of a compound of the formula:

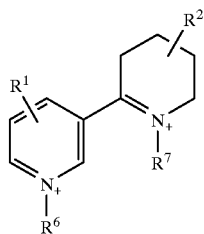

or a pharmaceutically acceptable salt thereof, wherein $R^1$, $R^6$, and $R^7$ are hydrogen or $C_1$–$C_4$ alkyl; and $R^2$ is =CHX, =CCH$_3$X, or =CHCH=CHX, wherein X is

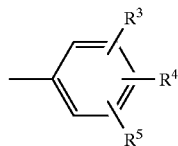

wherein $R^3$, $R^4$, and $R^5$ are selected from the group consisting of hydrogen, $C_1$–$C_4$ alkyl optionally substituted with N,N-dialkylamino having 1 to 4 carbons in each of the alkyls, $C_1$–$C_6$ alkoxy optionally substituted with N,N-dialkylamino having 1 to 4 carbons in each of the alkyls, carboalkoxy having 1 to 4 carbons in the alkoxy, amino, amido having 1 to 4 carbons in the acyl, cyano, N,N-dialkylamino having 1 to 4 carbons in each of the alkyls, halo, hydroxyl, and nitro.

Preferably, $R^2$ is attached to the 3-position of the tetrahydropyridine ring and $R^3$, which is preferably attached to the 4-position of the phenyl ring, is selected from the group consisting of amino, hydroxyl, chloro, cyano, dimethylamino, methyl, methoxy, isopropoxy, and nitro, with hydroxyl, isopropoxy, amino, acetylamino, acetoxy, and methoxy being particularly preferred. Another preferred embodiment is this method employing the compound such that $R^1$ and $R^5$ are both hydrogen, $R^3$ is methoxy, and $R^4$ is hydroxyl or methoxy. It may be desirable to have $R^3$ and $R^4$ attached to either the 4-or 2- position of the phenyl ring. Another example of a preferred compound employed in the methods described in this invention is wherein $R^1$ is hydrogen, $R^3$, $R^4$ and $R^5$ are all methoxy or wherein $R^3$ is 4-dimethylamino, and $R^4$ and $R^5$ are both hydrogen.

Thus, the present invention encompasses a method of treating tobacco-withdrawal symptoms comprising administering to an animal in need thereof a therapeutically effective amount of a benzylidene-anabaseine or a cinnamylidene-anabaseine capable of selectively activating alpha7 receptors, or a pharmaceutically acceptable salt thereof. Examples of benzylidene-anabaseine or a cinnamylidene-anabaseine capable of selectively activating alpha7 receptors include, but are not limited to, 3-(2,4dimethoxybenzylidene) anabaseine, 3-(4-hydroxybenzylidene) anabaseine, 3-(4methoxybenzylidene) anabaseine, 3-(4-aminobenzylidene) anabaseine, 3-(4-hydroxy-2methoxybenzylidene) anabaseine, 3-(2-hydroxy-4-methoxybenzylidene) anabaseine, 3(4-isopropoxybenzylidene) anabaseine, (7'-methyl-3-(2,4-dimethoxybenzylidene)) anabaseine, 3-(4-acetylaminocinnamylidene) anabaseine, 3-(4-hydroxycinnamylidene) anabaseine, 3-(4-methoxycinnamylidene) anabaseine, 3-(4-hydroxy-2-methoxycinnamylidene) anabaseine, 3-(2,4-dimethoxycinnamylidene) anabaseine, and 3-(4acetoxycinnamylidene) anabaseine.

As used herein "capable of selectively activating alpha7 receptors" means compounds that activate nicotinic alpha7 receptors without appreciably activating other receptor subtypes such as alpha4beta2 receptors.

Another aspect of this invention comprises a method of stimulating brain alpha7 receptors antagonized by ethanol in a mammal, comprising administering to an animal in need thereof a therapeutically effective amount of a compound of the formula:

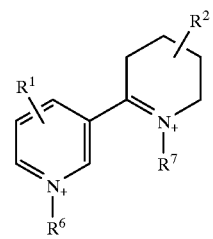

or a pharmaceutically acceptable salt thereof, wherein $R^1$, $R^6$, and $R^7$ are hydrogen or $C_1$–$C_4$ alkyl; and $R^2$ is =CHX, =CCH$_3$X, or =CHCH=CHX, wherein X is $R^3$

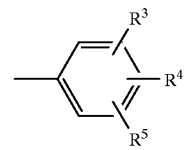

wherein $R^3$, $R^4$, and $R^5$ are selected from the group consisting of hydrogen, $C_1$–$C_4$ alkyl optionally substituted with N,N-dialkylamino having 1 to 4 carbons in each of the alkyls, $C_1$–$C_6$ alkoxy optionally substituted with N,N-dialkylamino having 1 to 4 carbons in each of the alkyls, carboalkoxy having 1 to 4 carbons in the alkoxy, amino, amido having 1 to 4 carbons in the acyl, cyano, N,N-dialkylamino having 1 to 4 carbons in each of the alkyls, halo, hydroxyl, and nitro.

The present invention also encompasses a method of protecting against cell loss induced by ischemia in a mammal, comprising administering to an animal in need thereof a therapeutically effective amount of a compound of the formula:

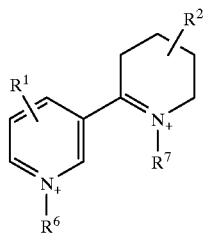

or a pharmaceutically acceptable salt thereof, wherein $R^1$, $R^6$, and $R^7$ are hydrogen or $C_1$–$C_4$ alkyl; and $R^2$ is =CHX, =CCH$_3$X, or =CHCH=CHX, wherein X is

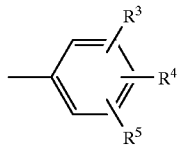

wherein $R^3$, $R^4$, and $R^5$ are selected from the group consisting of hydrogen, $C_1$–$C_4$ alkyl optionally substituted with N,N-dialkylamino having 1 to 4 carbons in each of the alkyls, $C_1$–$C_6$ alkoxy optionally substituted with N,N-dialkylamino having 1 to 4 carbons in each of the alkyls, carboalkoxy having 1 to 4 carbons in the alkoxy, amino, amido having 1 to 4 carbons in the acyl, cyano, N,N-dialkylamino having 1 to 4 carbons in each of the alkyls, halo, hydroxyl, and nitro. The cell loss may be caused by a stroke or by glutamate-induced excitotoxicity. Thus, this invention includes a method of protecting against cell loss induced by ischemia comprising administering to an animal in need thereof a therapeutically effective amount of a benzylidene-anabaseine or a cinnamylidene-anabaseine capable of selectively activating alpha7 receptors, or a pharmaceutically acceptable salt thereof.

The invention also encompasses a method of prophylaxis against cell loss from focal ischemic insult, comprising administering to a mammal an amount of an alpha7 nicotinic agonist before occurrence of ischemia in an amount effective to protect against the cell loss. Preferred alpha7 nicotinic agonists comprise a benzylidene-anabaseine or a cinnamylidene-anabaseine.

Further embodiments of the invention also comprise a method of treating age related learning or memory impairment comprising administering to an animal in need thereof a therapeutically effective amount of a cinnamylidene-anabaseine.

3.0 BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1. Shows 3-(2,4-Dimethoxybenzylidene) anabaseine (also known as "DMB" or "GTS-21"), a model for benzylidene-anabaseines with alpha7 selective nicotinic agonist activity. Other 3-(benzylidene)anabaseines are identical except for different substituents on the benzylidene moiety.

Figure 2:
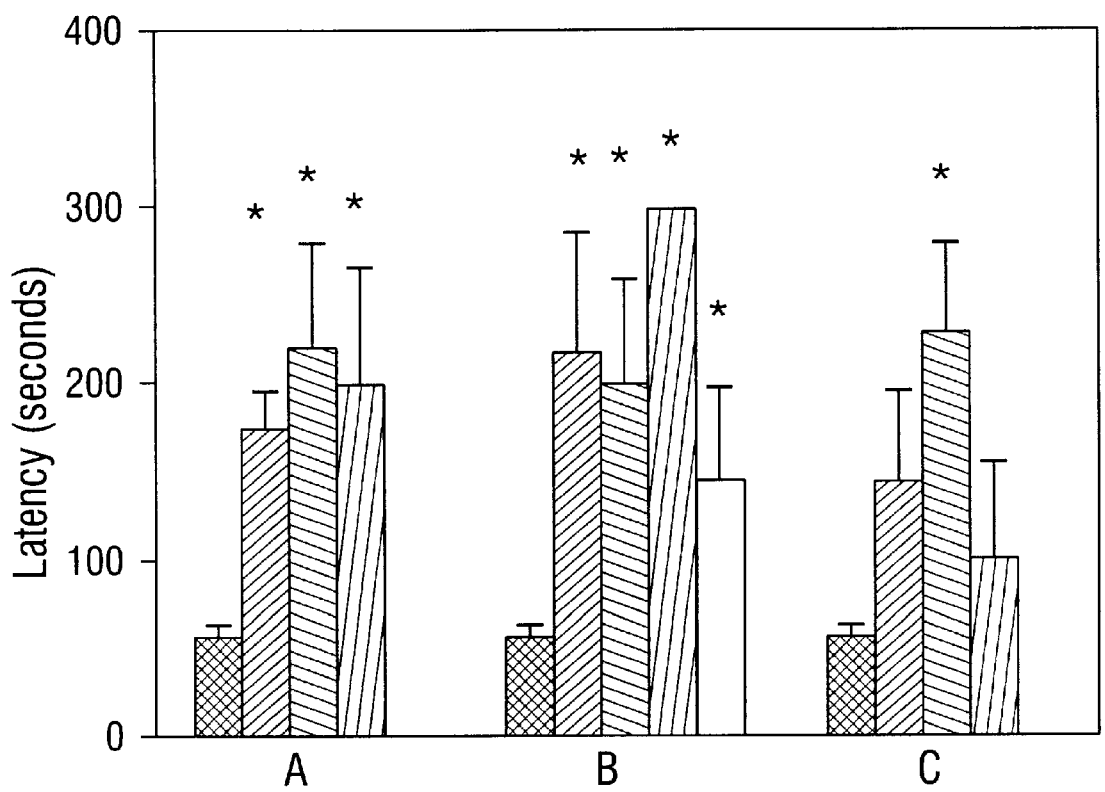

FIG. 2. Shows the effect of cinnamylidene-anabaseines on passive avoidance behavior in rats that received bilateral nucleus basalis lesions. The unlesioned control valve was 247≠35 Sec mean±. (A) is 3-cinnamylidene anabaseine; (B) is 3(methoxy cinnamylidene) anabaseine; (C) is 3-(4-methoxy-cinnamylidene) anabaseine. Dosages are IP in mg/kg where ■ is O, # is 0.1; is 0.2; is 1.0 and is 3.0 mg/kg. indicates that p<0.05 compared to saline control one way ANOVA. All values are mean ±SEM (n=4–6/group).

Figure 3:
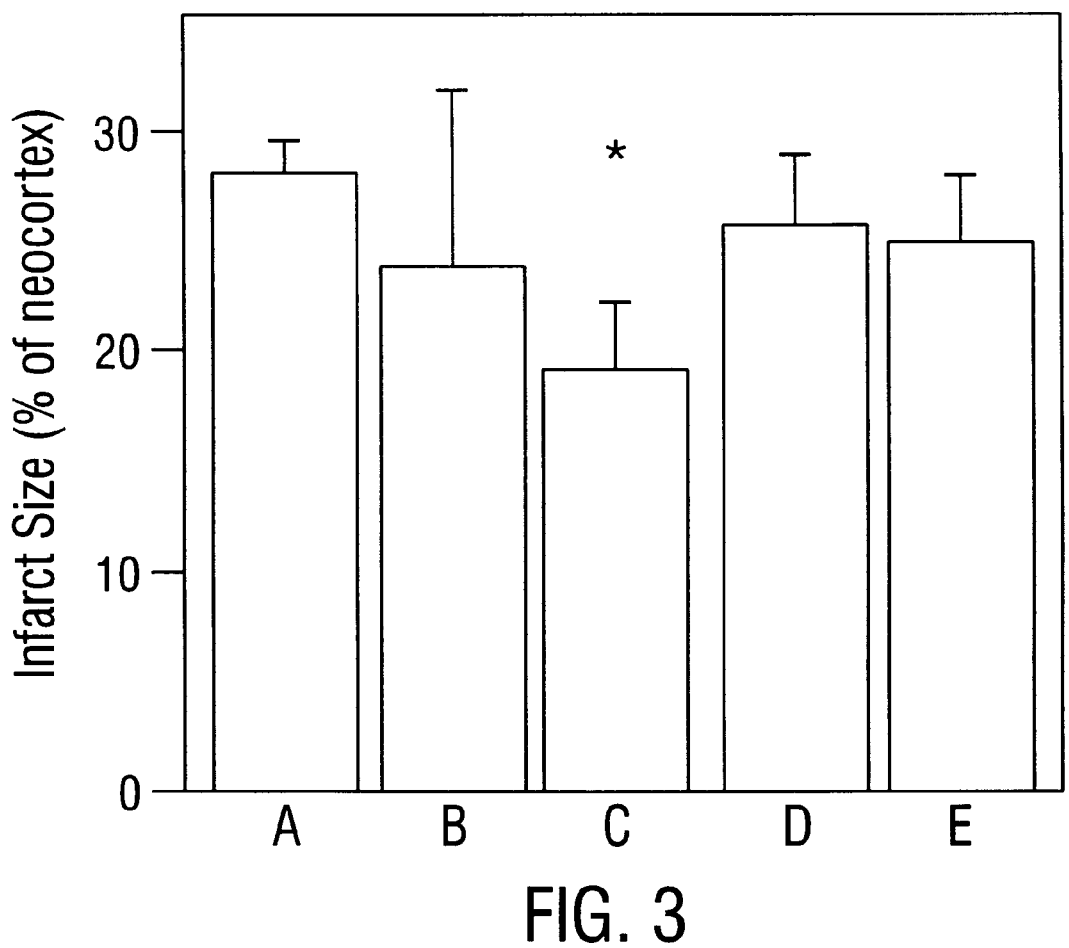

FIG. 3. Shows the effects of cerebral ischemia (stroke) on brain cell death, and the ability of the benzylidene-anabaseine alpha7 nicotinic agonist to protect against this cell death. Rats received a 30 minute ischemia attack through tying of their common carotid; the amount of cell death (proportional to Infarct Size) was determined 24 hours later. Some animals received the benzylidene-anabaseine compound DMXB (1 mg/kg IP, salt weight) 1 hour before ligation, or the nicotinic antagonist mecamylamine (0.5 mg/kg IP), or both mecamylamine and DMXB, or DMXB 5 minutes after the ligation. Only DMXB alone, given before ligation, protected against cell loss (*p<0.05 compared to saline injected controls; one way ANOVA, n=4–5/group).

Figure 4:
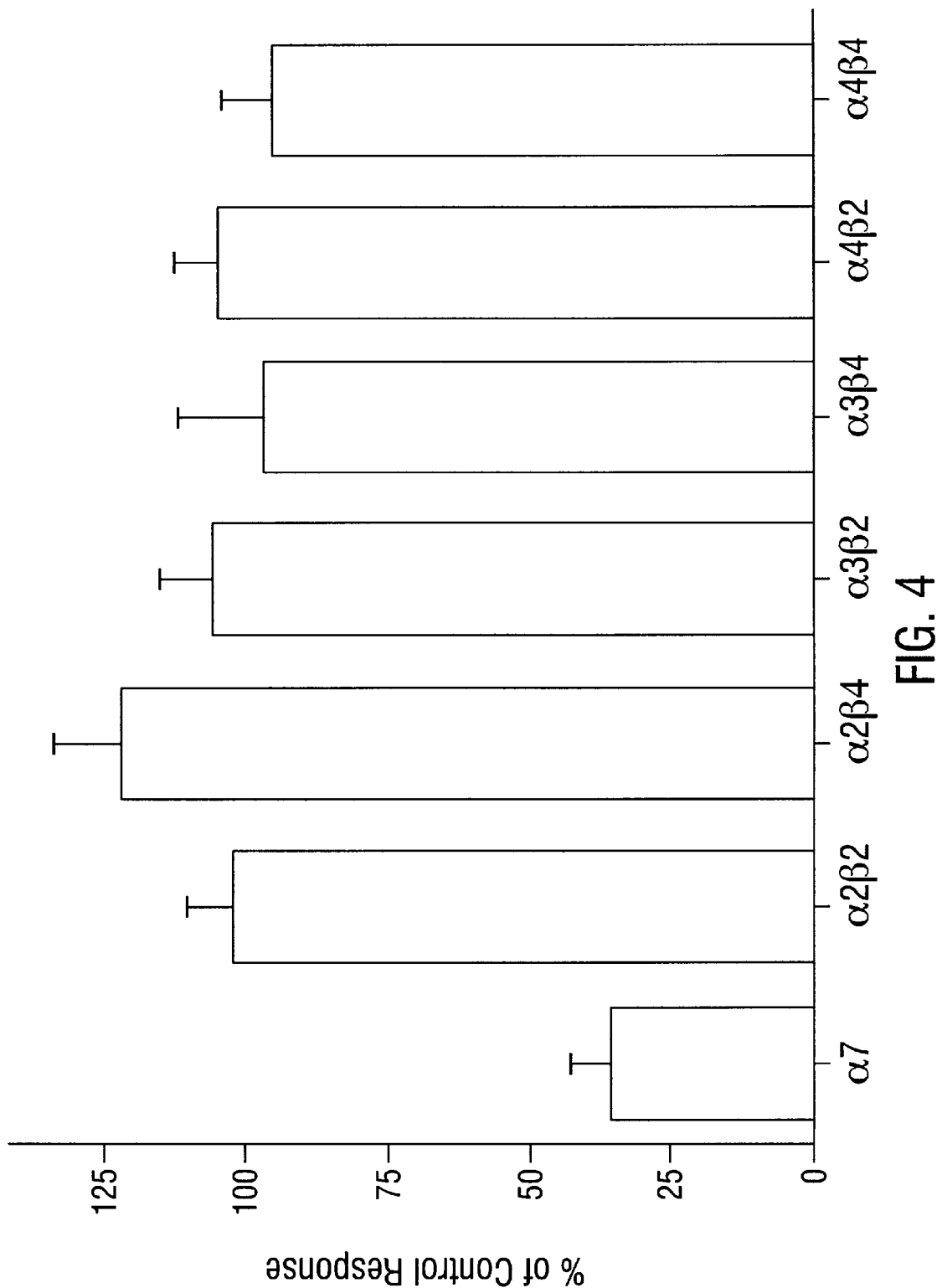

FIG. 4. Shows the effects of 100 mM ethanol on the responsiveness of n-acetylcholine receptor subtypes to an EC50 concentration of nicotine.

Figure 5:
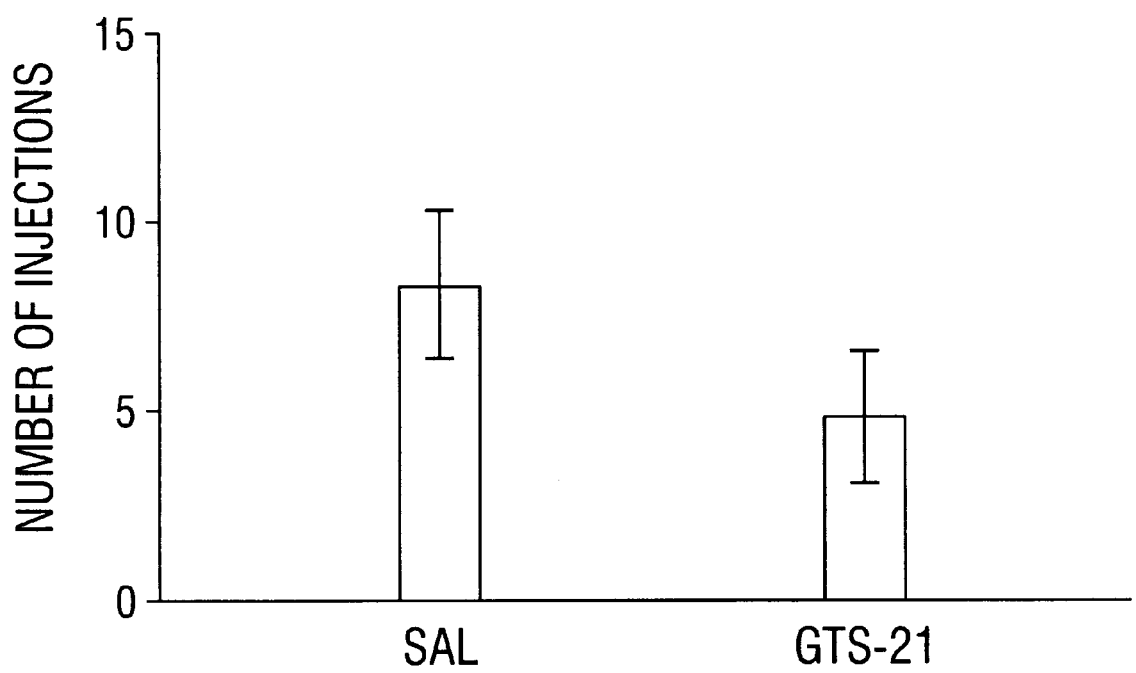

FIG. 5. Shows the inhibition of nicotine self-administration in rats by the injection of DMXB (GTS-21), as compared to injection of the control of saline.

Figure 6A:
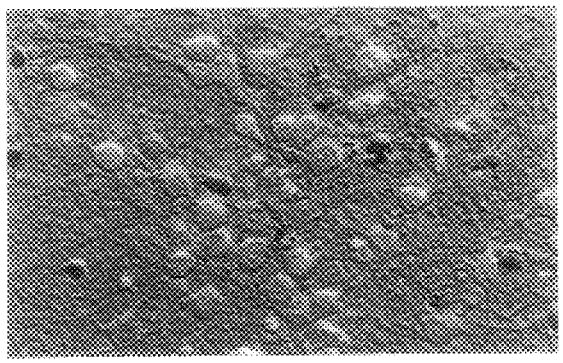

FIG. 6A. Effects of DMXB on EAA-induced cytotoxicity in cultured neocortical neurons. No treatment.

Figure 6B:
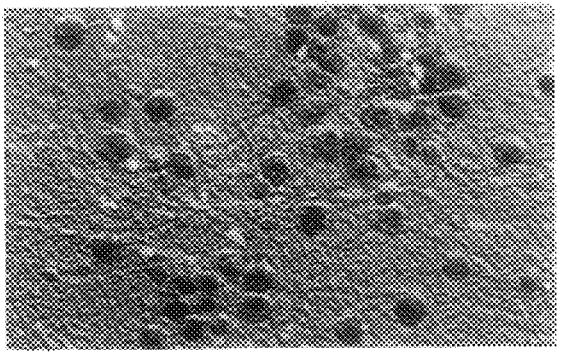

FIG. 6B. As in FIG. 6A, cells incubated with 1 mM glutamate for 10 min, and then after washout glutamate for 1 hr.

Figure 6C:
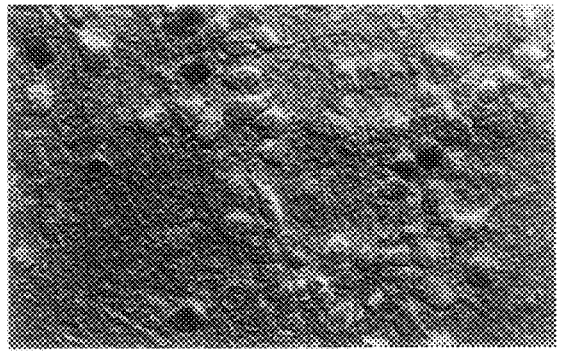

FIG. 6C. As in FIG. 6A, cells exposed to 10 $\mu$M DMXB for 24 hr prior to glutamate treatment.

Figure 6D:
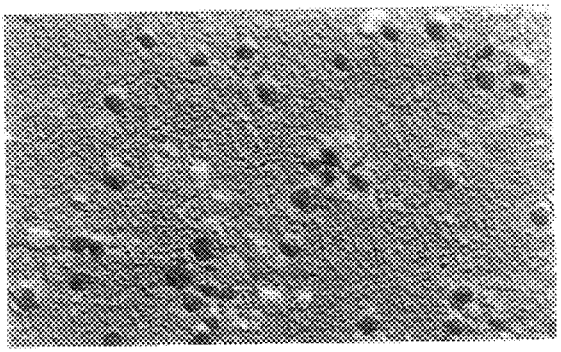

FIG. 6D. As in FIG. 6A, cells exposed to co-application of 10 $\mu$M DMXB and 1 nM α-bungarotoxin prior to glutamate treatment. Scale bar, 50 $\mu$m.

Figure 6E:
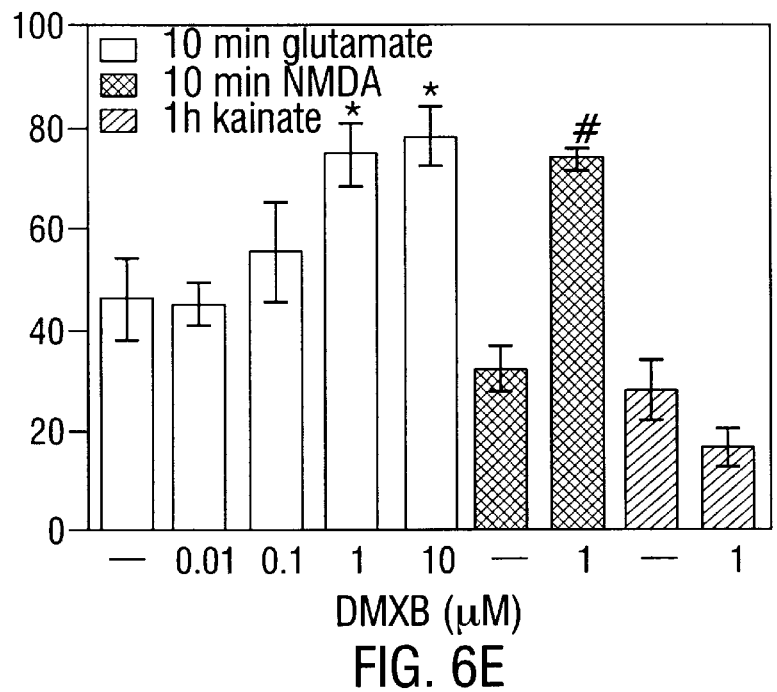

FIG. 6E. Inhibition of neurotoxicity by DMXB pretreatment. After 24 hr exposure to DMXB, 1 mM EAA was added for 10 min or 1 hr followed by EAA-free for 1 hr, or not, respectively. % of control is the ratio of viable cells with EAA exposure to those without.

Figure 6F:
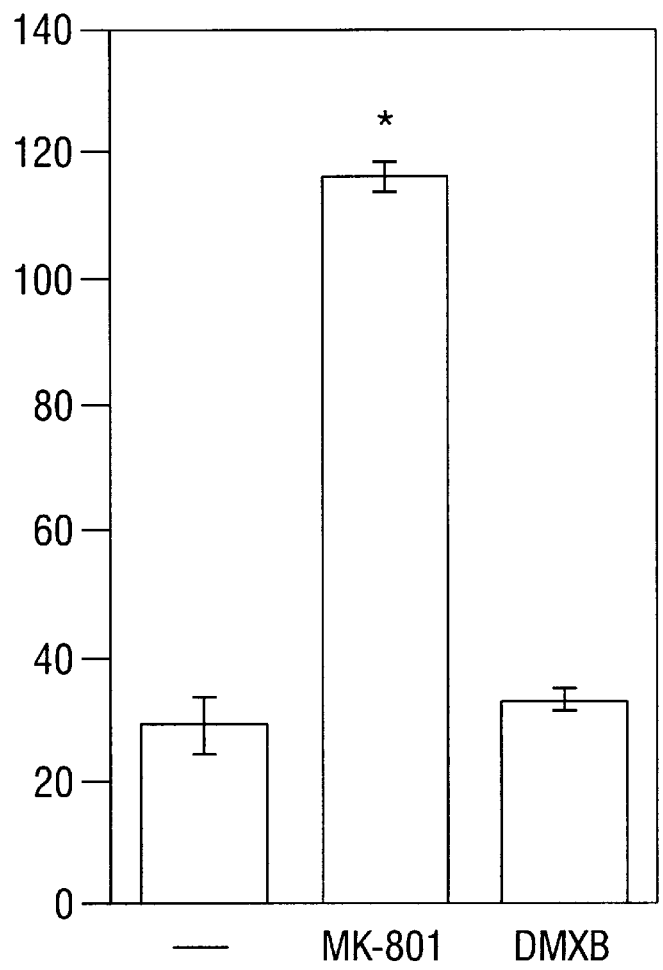

FIG. 6F. DMXB or MK 801 (10 $\mu$M each, was applied simultaneously with 1 mM glutamate for 10 min. * and # refer to p<0.05 from glutamate or NMDA alone, respectively. Values reflect mean±SEM (n=5).

Figure 7:
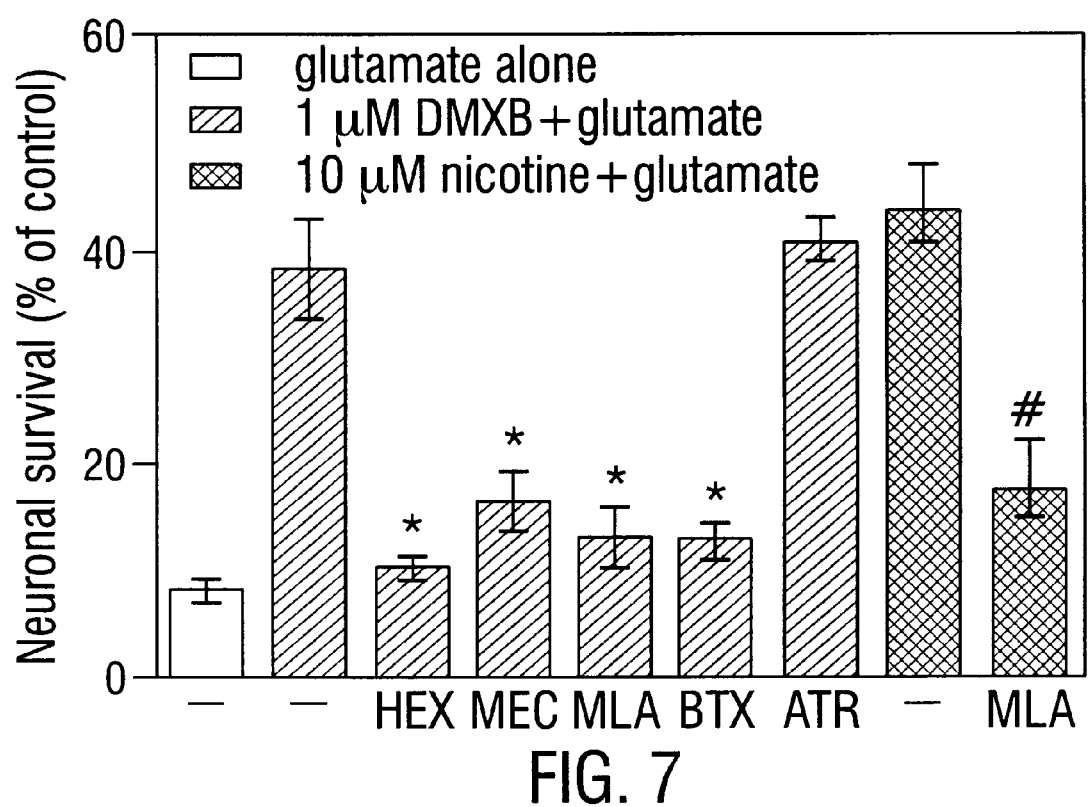

FIG. 7. Effects of cholinergic antagonists on DMXB-induced protection from glutamate cytotoxicity. Each antagonist was added to medium containing 1 $\mu$M DMXB or 10 $\mu$M nicotine for 24 hr. HEX, 1 $\mu$M hexamethonium. MEC, 1 $\mu$M mecamylamine. MLA, 10 nM methyllycaconitine. BTX, 1 nM (alpha)-bungarotoxin. ATR, 1 $\mu$M atropine. * and # denote p<0.05 compared to DMXB or nicotine alone, respectively (n=5).

Figure 8A:
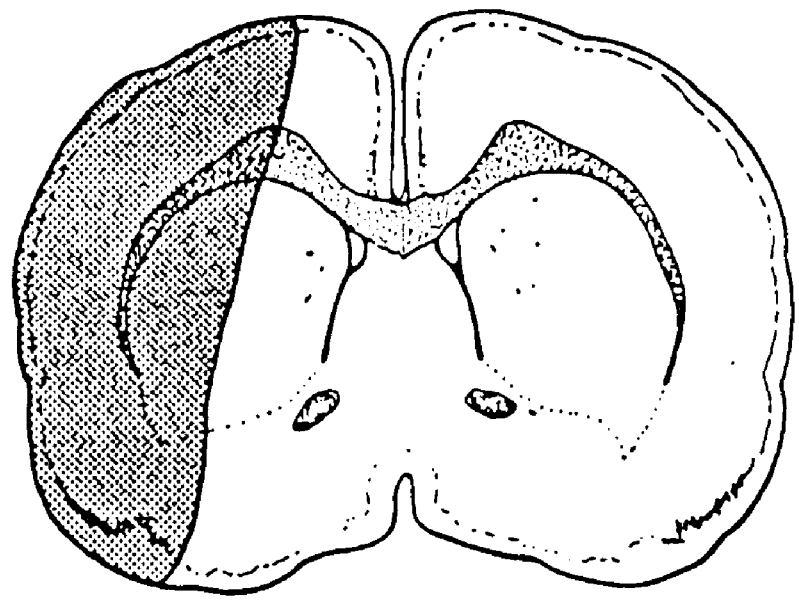
Figure 8A:
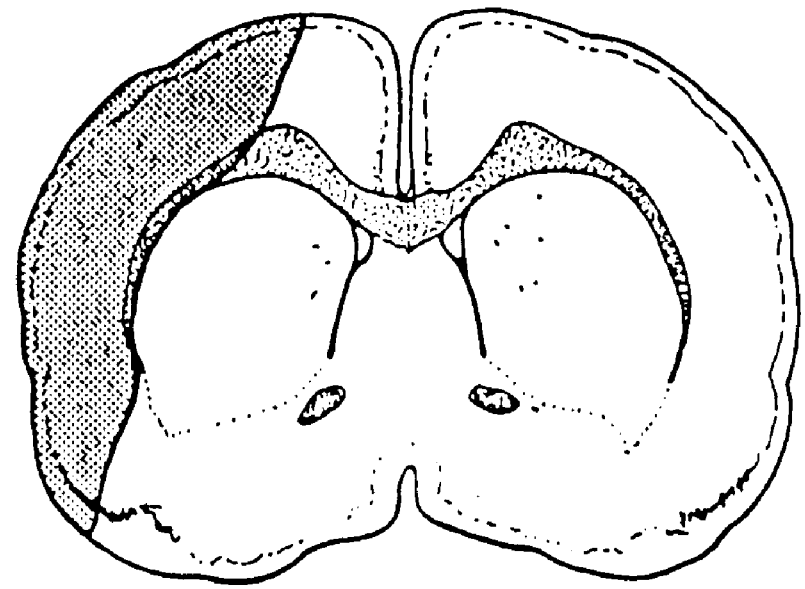

FIG. 8A. Effects of DMXB on infarct size following focal ischemic insult. Coronal section 5 mm posterior to frontal pole, where infarct size was maximal. Shaded region is from typical stained saline-injected animal with 28% infarct (mean value). Bottom: Coronal section, same coordinates, of DMXB-treated animal with 19% infarct (mean value).

Figure 8B:
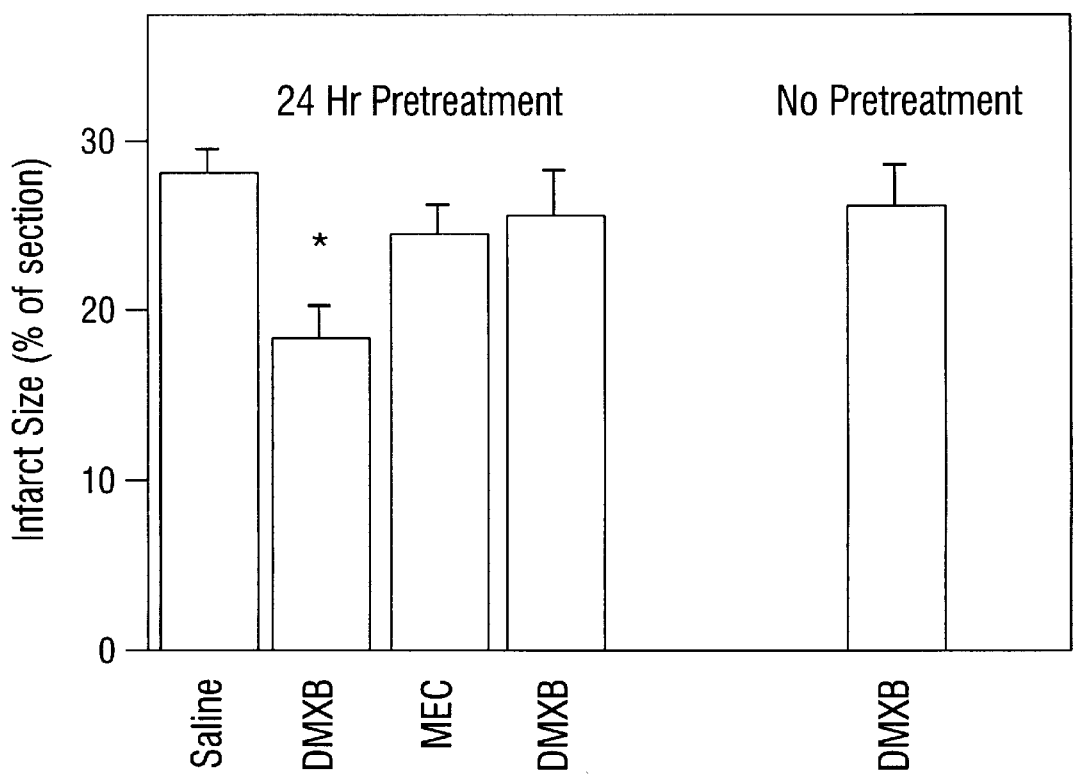
Figure 9A:
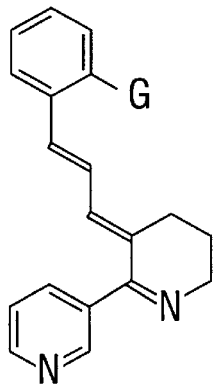
Figure 9B:
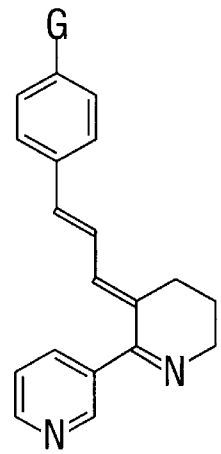
Figure 9C:
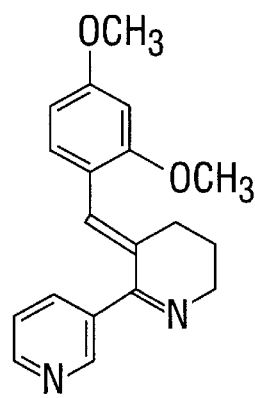

FIG. 8B. Effects of DMXB on infarct size following focal ischemic insult. Infarct sizes as fraction of total coronal area at 5 mm posterior to frontal pole. Drugs were injected 24 hr before ischemia. MEC: 0.5 mg/kg IP mecamylamine; DMXB: 1 mg/kg IP. Right panel: DMXB injected during ischemia, *p<0.05-compared to saline injected; one way ANOVA)(n=6–8) FIG. 9. Comparison of cinnamylidine structures with a benzylidene (GTS-21).

Figure 10:
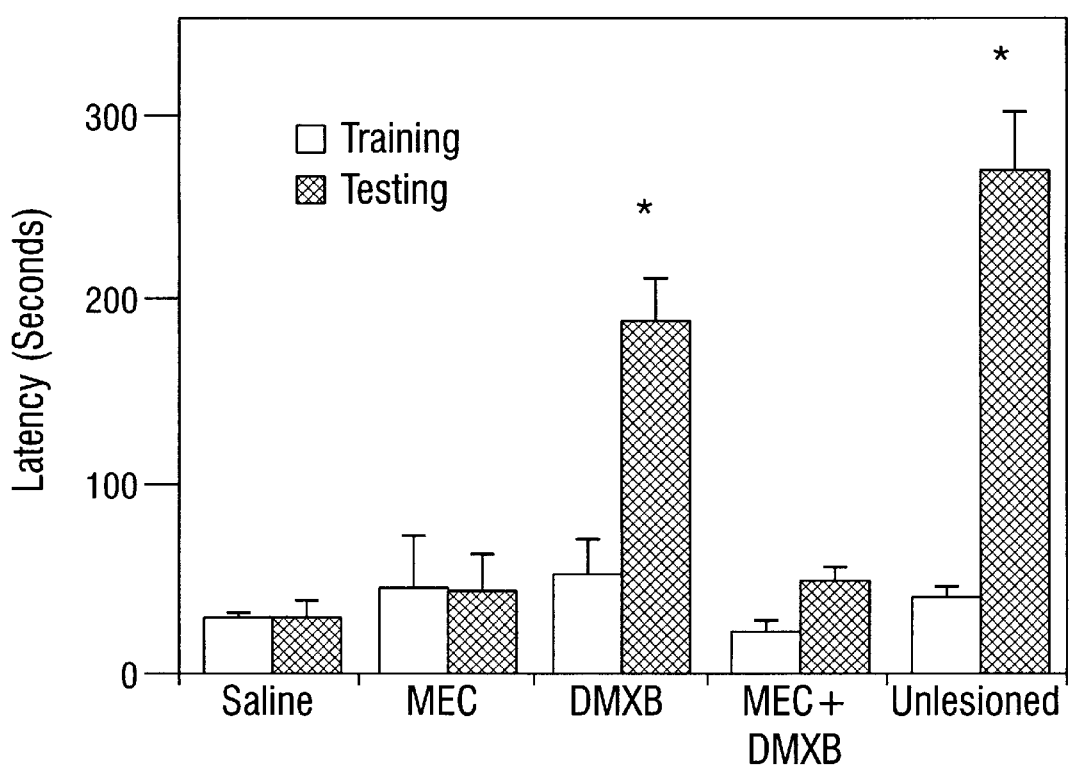

FIG. 10. Effects of mecmylamine on DMXB-induced improvement in passive avoidance behavior. Adult Sprague Dawley albino rats were bilaterally nucleus basalis-lesioned and tested for passive avoidance behavior 1 month later as described in the text. Latencies for training and testing intervals were determined 15 min after IP injection of saline vehicle, 0.5 mg/kg DMXB, 0.2 mg/kg mecamylamine (MEC) or both drugs, and described as mean±SEM of 5 animals/group. *$p<0.05$ compared to saline injected group, one way ANOVA.

Figure 11A:
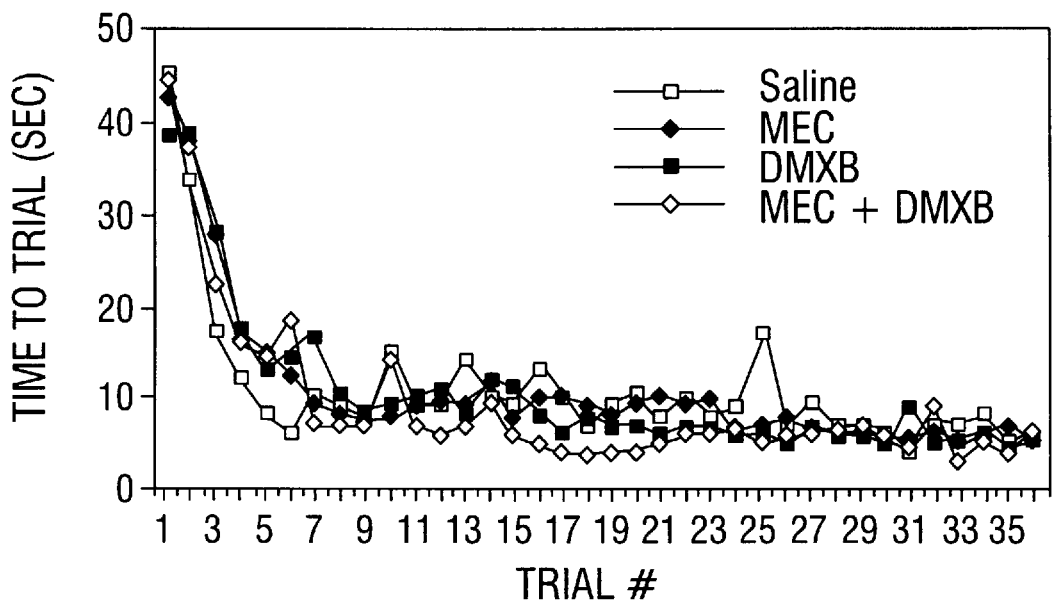
Figure 11B:
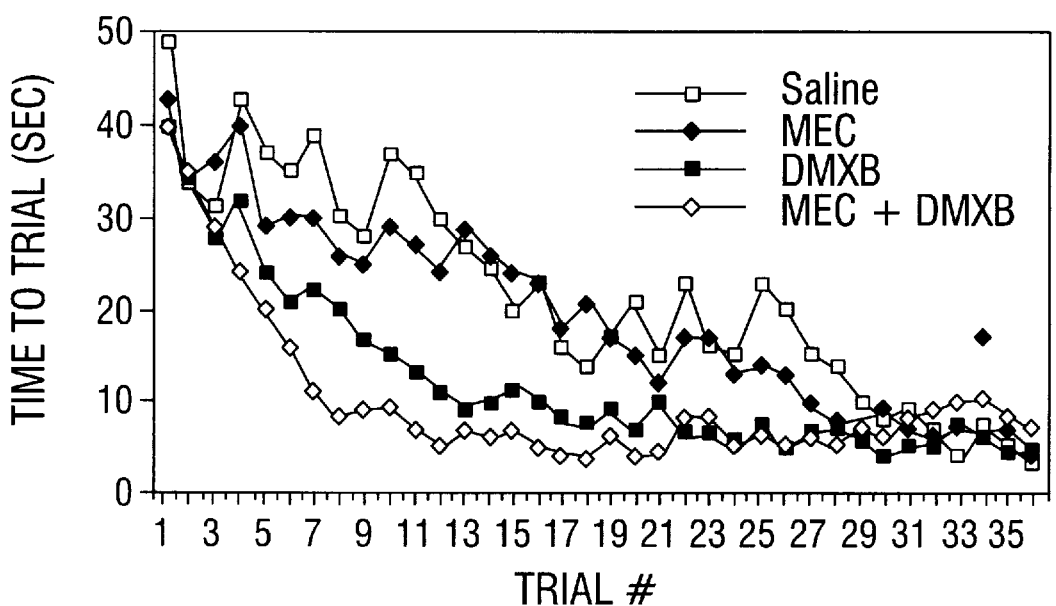

FIG. 11. Effects of DMXB on training in the Morris water task in bilaterally nucleus basalis lesioned rats. Animals that were lesioned or sham-operated began training one month later as described in the text. Saline diluent, 0.5 mg/kg DMXB, 0.2 mg/kg mecamylamine (MEC), or both drugs were injected IP 15 min prior to the first trial each day in the lesioned and unlesioned groups. Values are the mean times necessary to find the target (maximum: 60 sec) (N=5). Intergroup comparisons are described in Table 1.

Figure 12:
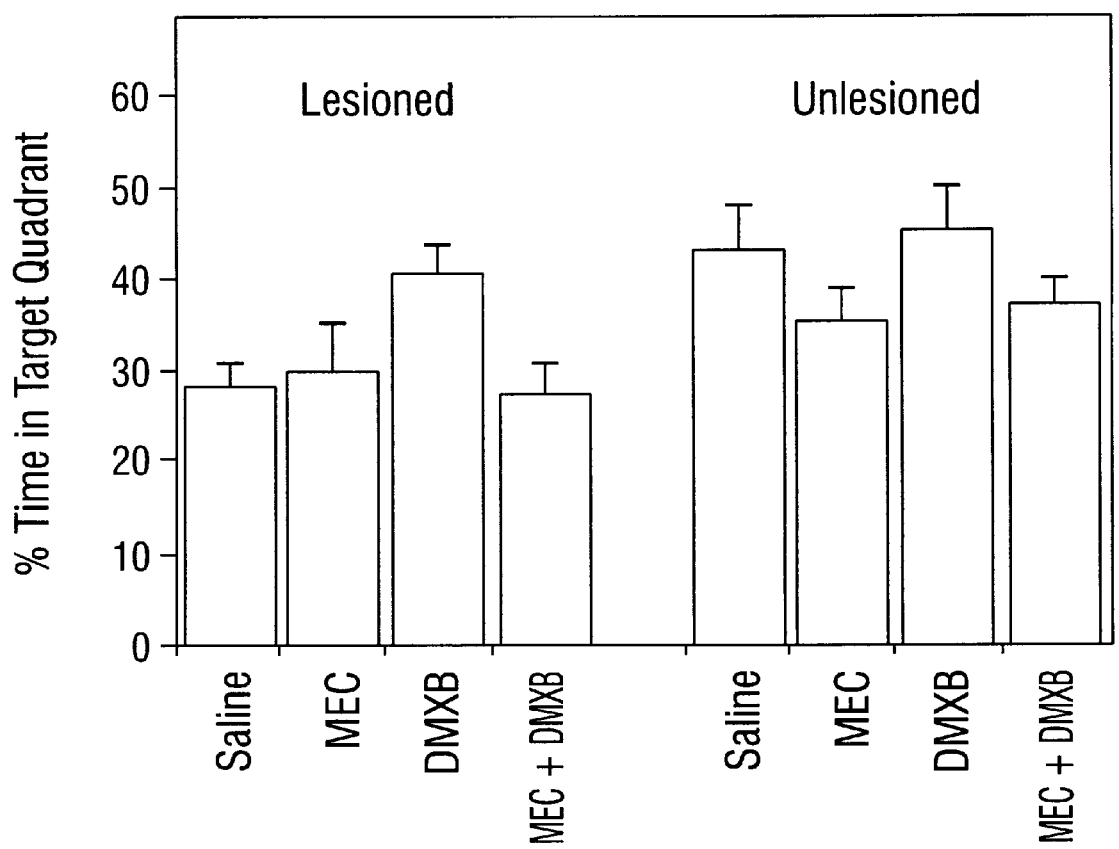

FIG. 12. Effects of DMXB on trial performance in the Morris water task in bilaterally nucleus basalis lesioned rats. Animals were lesioned, trained and injected as described in FIG. 3. The fraction of time spent in the target quadrant during the 60 sec trial interval on day 4 was determined for each group, and expressed as the mean±SEM of 5 animals/group. *$p<0.05$ compared to lesioned group injected with saline (one way ANOVA).

Figure 13B:
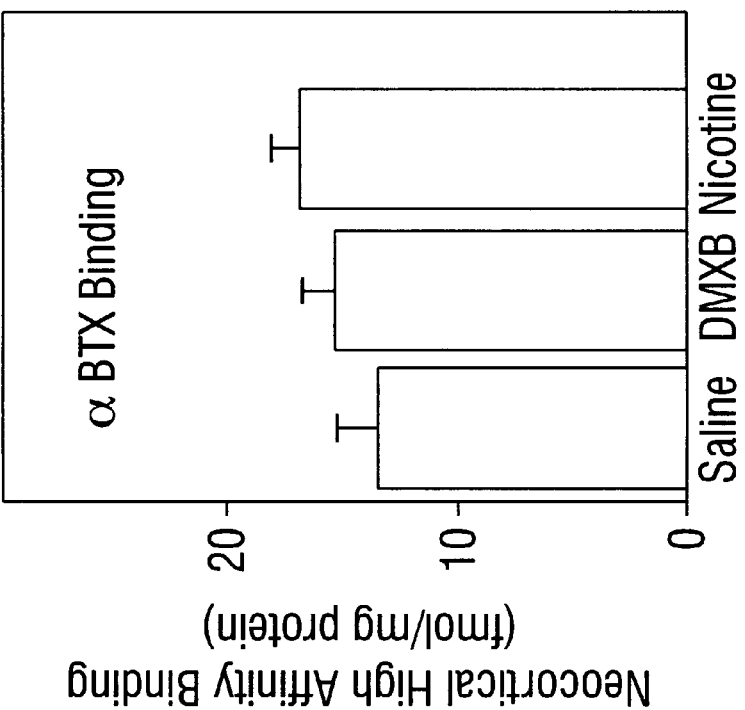
Figure 13A:
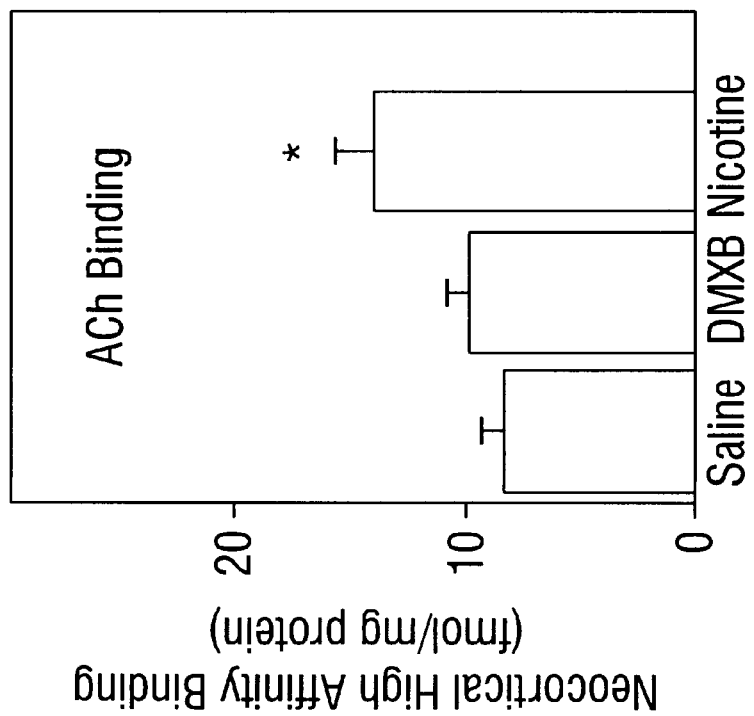

FIG. 13A. Effects of chronic injections of DMXB or nicotine on high affinity [$^3$H]ACh or [$^{125}$I]α-bungarotoxin (BTX) binding in rat neocortices. Adult male rats were injected with saline vehicle, 1 mg/kg DMXB or 0.2 mg/kg nicotine (NIC) (IP) daily for 2 weeks. At that time, neocortices were removed and assayed for high affinity [$^3$H]ACh or [$^{125}$I]α-bungarotoxin binding as described in the text. Each value is the mean±SEM of 4 animals/group; *$p<0.05$ compared to saline injected control value (one way ANOVA). Responses of rat α7 ACHR to 3-CA, 2-MeOCA and 4-MeOCA. Concentration-response relationships for the peak agonist activated currents of oocytes injected with RNA coding for the rat α7 subunit. All responses were initially measured relative to the individual oocyte-response to 500 μM ACh, applied 5 min prior to drug-application. Responses were normalized relative to the maximum response obtainable with ACh so that a response of 1 represents full efficacy. The ratio of 500 μM ACh control response to ACh maximum was taken from Papke et al., 1997.

FIG. 13B. Effects of chronic injections of DMXB or nicotine on high affinity [$^3$H]ACh or [$^{125}$I]α-bungarotoxin (BTX) binding in rat neocortices. Adult male rats were injected with saline vehicle, 1 mg/kg DMXB or 0.2 mg/kg nicotine (NIC) (IP) daily for 2 weeks. At that time, neocortices were removed and assayed for high affinity [$^3$H]ACh or [$^{125}$I]α-bungarotoxin binding as described in the text. Each value is the mean±SEM of 4 animals/group; *$p<0.05$ compared to saline injected control value (one way ANOVA). Responses of rat α7 AChR to 3-CA, 2-MeOCA and 4-MeOCA. Residual inhibition of control (500 μM) ACh resonses of rat α7 injected oocytes after the application of 3-CA, 2-MeOCA or 4-MeOCA at specified concentrations. All responses are expressed relative to the oocyte-response to 500 μM ACh applied 5 min prior to the experimental agonist application.

Figure 14A:
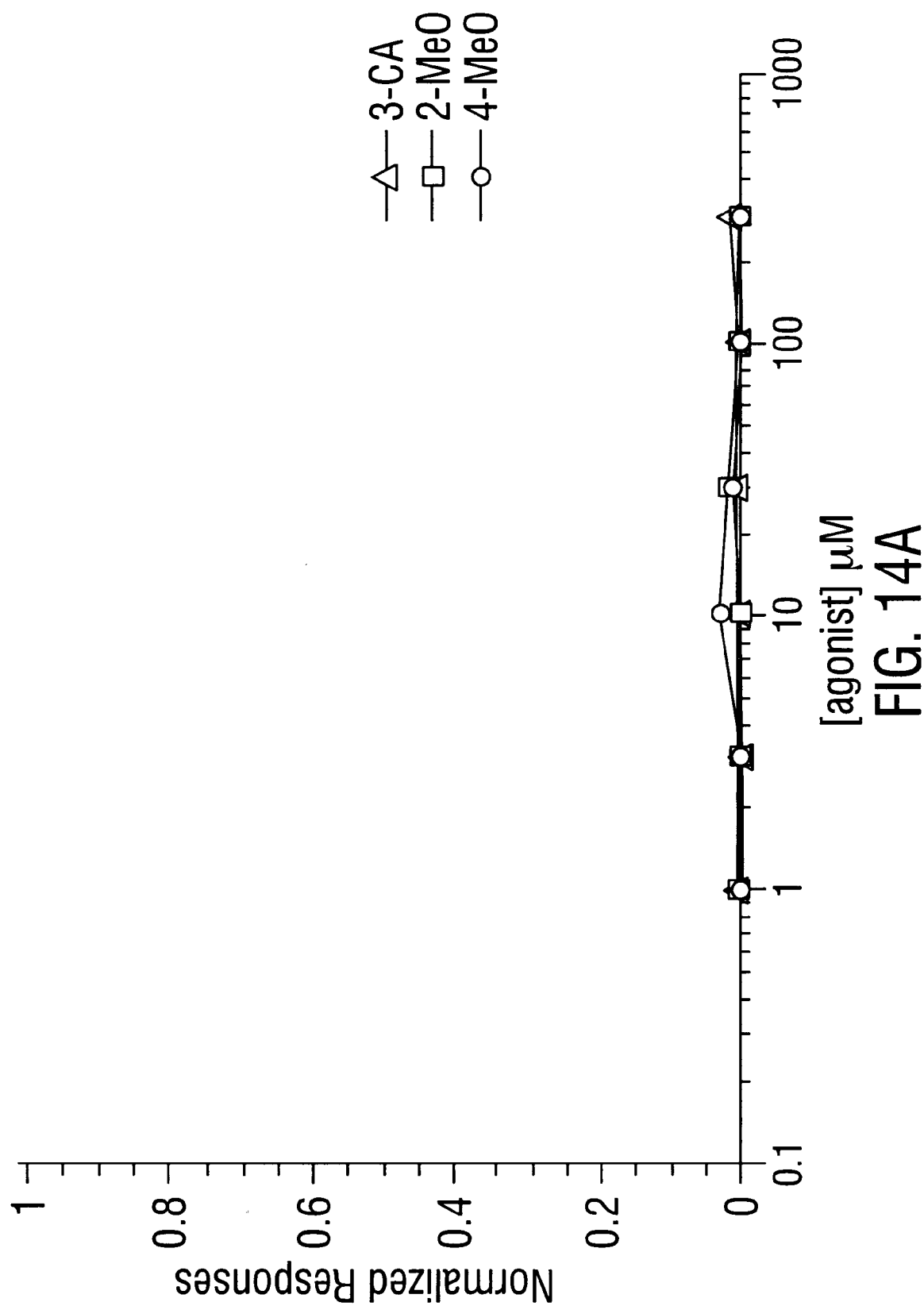

FIG. 14A. Responses of α4β2 ACHR to 3-CA, 2-MeOCA or 4-MeOCA. Concentration-response relationships for the peak agonist activated currents of oocytes injected with RNA coding for rat α4β2 subunits. Responses are first expressed relative to the response to 10 μM ACh, applied 5 min before drug-application, then normalized to the maximum response obtainable with ACh so that a response of 1 represents full efficacy. The ratio between 10 μM ACh and maximum ACh response was determined in separate experiments.

FIG. 14B. Responses of α4β2 AChR to 3-CA, 2-MeOCA or 4-MeOCA. Residual inhibition of control (10 μM) ACh responses of rat α4β2 injected oocytes after application of 3-CA, 2-MeOCA or 4-MeOCA at the specified concentration. Responses are expressed relative to the individual oocyte-response to 10 μM ACh, applied 5 min prior to experimental agonist application.

Figure 15:
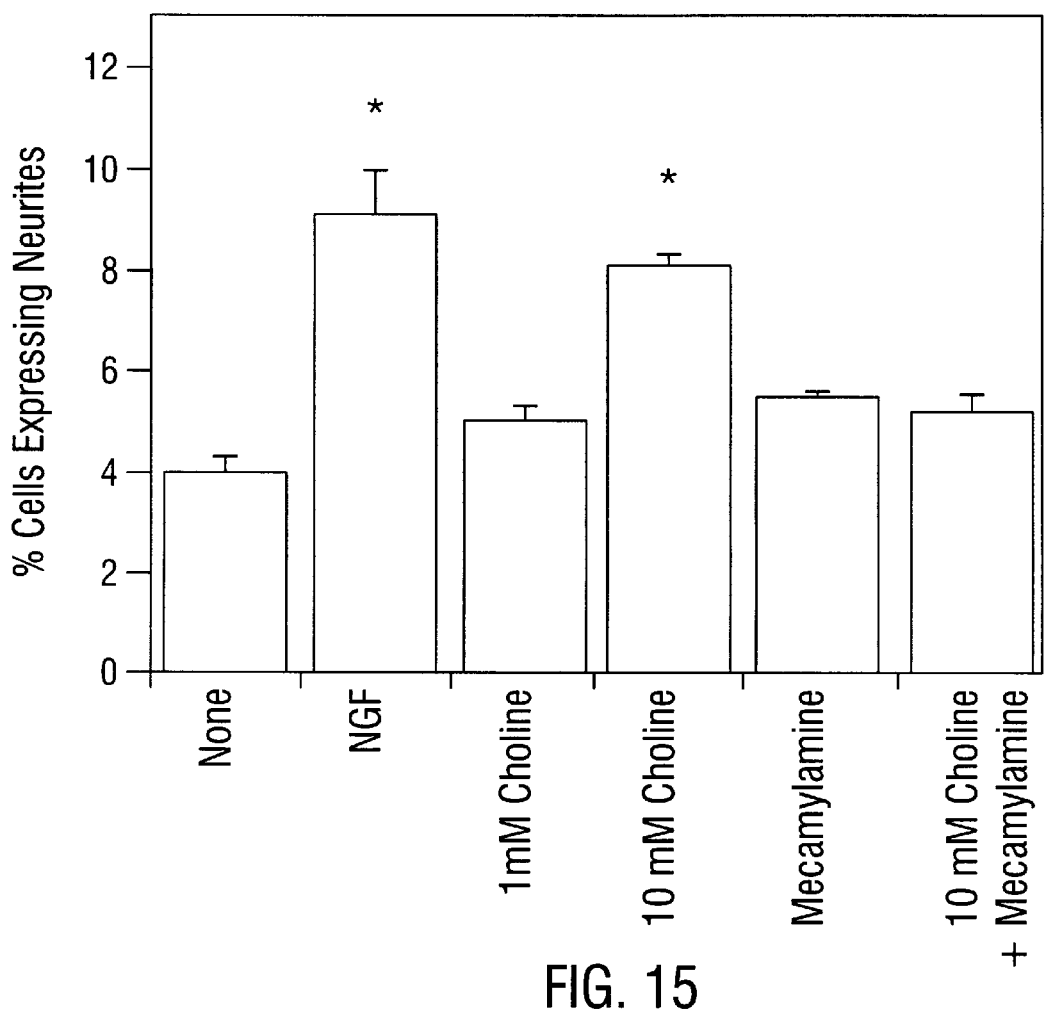

FIG. 15. Effects of choline on neuite-viability in differentiated PC12 cells under NGF-deprivation. PC12 cells that had differentiated for 1 week and then deprived of NGF+ serum were exposed for 4 days to serum-free medium with or without 100 ng/ml NGF, the specified choline concentration ±10 ul mecamylamine. The fraction of PC12 cells expressing neurites at that time was quantified and expressed as the mean±SEM of 3–4 plates/group, * $p<0.05$ compared to untreated cells (one way ANOVA).

4.0 DESCRIPTION OF ILLUSTRATIVE EMBODIMENTS

The selective activation of alpha7, as opposed to alpha4beta2, nicotinic receptors, by benzylidene- and cinnamylidene-anabaseines as illustrated in the specific examples, has led to the development of several potential therapeutic uses in a variety of conditions associated with effects on alpha7 nicotinic receptors. Thus the benzylidine and cinnamylidine-anabaseines are useful in alleviating symptoms associated with tobacco withdrawal and alcohol consumption, protection from ischemia and stroke, and treatment of age related learning and memory impairment.

Nicotinic alpha7 receptor activation is one component of the effects of tobacco/nicotine that make it difficult to withdraw. The selective targeting of nicotinic receptor subtypes, such as the alpha7 subtype, in tobacco cessation therapy is expected to provide therapies which block withdrawal symptoms without producing direct reinforcement. Such treatments may prove to be more effective than therapies with nicotine-containing gum or patches because craving may not be prolonged in recovering smokers.

There is no evidence that alpha7 receptors induce nicotine craving in rat or other species. Alpha-bungarotoxin does not appear to block the reinforcing action of nicotine, so this action is apparently not alpha7 mediated. Therefore, the anabaseines of the present invention, by virtue of their ability to activate alpha7 receptors selectively (Table 1), are expected to reduce withdrawal symptoms without reinforcing the addictive behavior.

Moreover, the alpha4beta2 antagonist properties of these agents is expected to permit them to interfere with any addictive actions mediated by these receptors. Nicotine is highly potent at alpha4beta2 receptors, and these receptors normally upregulate with chronic nicotine exposure typical of addiction (Rowell and Li, 1997). Since benzylidene-and cinnamylidene-anabaseines stimulate a sub-group of the nicotine receptors activated by the nicotine itself, these compounds should prevent side-effects associated with tobacco withdrawal, without exhibiting the same pattern of addictive properties elicited by nicotine. The ability of the anabaseine and cinnamylidene-anabaseines herein disclosed to block alpha4beta2 receptors are expected to counteract the up-regulation of these receptors observed with chronic administration. This combination of alpha7 agonist and alpha4beta2 antagonist activity has a potentially a useful profile for helping patients to withdraw while not exerting reinforcing actions or withdrawal symptoms.

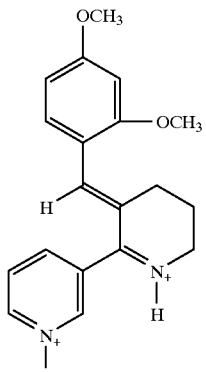

3-(2,4-Dimethoxybenzlidene)anabaseine ("DMXB" or "GTS-21"

While ethanol exerts many actions on a variety of brain proteins, the brain proteins activated by benzylidene- and cinnamylidene-anabaseines, such as nicotinic alpha7 receptors, are rendered hypofunctional by ethanol, placing them as prime sites for treating alcohol-induced intoxication and recovery from side effects associated with alcohol withdrawal. Anabaseines, such as DMXB, thus are expected to counteract the inhibitory activity of ethanol at these receptors, thereby attenuating ethanol's intoxicating properties.

A screening of different nicotinic receptor subtypes indicated that alpha7 nicotinic receptors were sensitive to antagonism by ethanol while other receptor types were not affected (FIG. 4). Activity at alpha7 receptors are therefore implicated in the intoxicating properties of ethanol, so that selective activation of alpha7 receptors is expected to be useful for preventing at least some of the effects of acute alcohol intoxication. Benzylidene- and cinnamylidene-anabaseines will be useful as a sober-up pill, as a therapy for withdrawal symptoms in alcoholics, and as a potential anti-intoxication medication.

Glutamate-release prompted by ischemia is a principle cause of neuronal loss in strokes. Glutamate is known to be a principle excitotoxin responsible for much of the cell death following ischemic attack Shimohama et al. (1994) demonstrated that nicotinic agonists may protect against glutamate-induced toxicity in brain neurons in vitro. The inventors reasoned that benzylidene- and cinnamylidene-anabaseine compounds might protect against cell death associated with ischemic attacks or stroke, as well as against glutamate-induced toxicities in brain.

In experiments with anabaseine compounds, the inventors demonstrated that such an effect is observed in vivo with a model alpha7 nicotinic agonist the prototypical benzylidene-anabaseine agent DMXB. The data show that DMXB protects against infarcts caused by cerebral ischemia in animals. Animals injected with 1 mg/kg DMXB 1 hour prior to focal ischemic insult did not have as much cell loss, as measured by infarct area, as did saline injected controls. Data suggested that the action was mediated by nicotinic receptors as indicated by the blocking action of mecamylamine injected with the DMXB (FIG. 3). These studies indicate that benzylidene- and cinnamylidene-anabaseines may be used prophylactically to prevent the damage observed in strokes and transient ischemic attacks, as well as other likely diseases associated with glutamate-induced excitotoxicity.

3-Cinnamylidene-anabaseine compounds were synthesized and found to exert activities on brain cells derived from their selective action on alpha7 nicotinic receptors that give them the following properties: 1) improvement in learning and memory related behaviors in animals otherwise rendered hypofunctional; 2) protection against brain cell death in several models relevant to Alzheimer's disease and stroke; 3) the ability to prevent ethanol induced intoxication mediated through nicotinic receptors, as well as reduced withdrawal symptoms associated with ethanol withdrawal; and 4) the ability to prevent withdrawal symptoms associated with tobacco withdrawal.

4.1 Pharmaceutical Compositions

The pharmaceutical compositions disclosed herein may be orally administered, for example, with an inert diluent or with an assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral prophylaxis the active compositions may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The phrase "pharmaceutically-acceptable" refers to molecular entities and compositions that do not produce an allergic or similar untoward reaction when administered to a human. The preparation of an aqueous composition that contains an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

The composition can be formulated in a neutral or salt form. Pharmaceutically-acceptable salts, include the acid addition salts and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug release capsules and the like.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

The following examples are included to demonstrate preferred embodiments of the invention. It should be appreciated by those of skill in the art that the techniques in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

5.0 EXAMPLES

5.1 Example 1—Receptor Binding Properties of Benzylidene-anabaseines

Benzylidene-anabaseine compounds (See FIG. 1) displaced high affinity alpha-bungarotoxin binding from rat brain membranes with higher affinity than nicotine dies (Table 1). The ability of benzylidene-anabaseines to act as agonists at alpha7 receptors but not at alpha4beta2 receptors was also demonstrated in oocytes. Each benzylidene-anabaseine activated alpha7 receptors compared to the endogenous transmitter acetylcholine (Table 1). In contrast, none of these agents elicited significant activation of alpha4beta2 receptors (Table 1). These agents also antagonized the alpha7 receptor and alpha4beta2 receptor, the former observation occurring after receptor-activation. Blockade of the alpha4beta2 receptor though observed at higher concentrations than alpha7 activation, may be important for therapeutic activity as well.

TABLE 1

Effects of Different 3-Benzylidene-Anabaseine Compounds on Alpha7 and Alpha4beta2 Receptor Activation

| Compound | alpha7 binding[1] | alpha7 activation[2] | alpha4beta2 activation[3] |
|---|---|---|---|
| DMXB | 52 | 0.2 | <0.01 |
| 3-(4-hydroxybenzylidene)anabaseine | 69 | 0.31 | 0.02 |
| 3-(4-methoxybenzylidene)anabaseine |  | 0.07 | 0.05 |
| 3-(4-aminobenzylidene)anabaseine (GTS-13) | 93 | 0.72 | 0.05 |
| 3-(4-hydroxy-2-methoxybenzylidene)anabaseine | 84 | 0.41 | 0.04 |
| 3-(4-methoxy-2-hydroxybenzylidene)anabaseine | 45 | 0.29 | 0.01 |
| 7'-methyl-DMXB |  | 0.32 | 0.02 |

[1] % Inhibition of high affinity alpha-bungarotoxin binding (1 nM) at a concentration of 1 μM.
[2] Response to rat alpha7 receptor activation in Xenopus oocytes at 20 μM of the drug, normalized to 500 μM acetylcholine (maximum response).
[3] Response to rat alpha4beta2 receptor activation in Xenopus oocytes at maximal concentration of drug, compared to maximal acetylcholine concentration.

5.2 Example 2—Preparation of 3-(4-isopropoxybenzylidene)anabaseine dihydrochloride ("GTS-85")

A mixture of 4-isopropoxybenzaldehyde (197 mg, 1.2 mmol), anabaseine (233 mg, 1mmol), 4 drops of concentrated HCl and 25 ml of absolute ethanol was refluxed for 6 hours. A yellow precipitate was obtained on adding 40 ml of ethyl acetate. The product was washed with ethyl acetate to remove the unreacted 4-isopropoxybenzaldehyde. Recrystallization from hot ethanol-ethyl acetate gave the 3-(4isopropoxybenzylidene) anabaseine dihydrochloride (310 mg, 68% yield). IH NMR (DMSO-$d_6$): 8.91($H_2'$, doublet, J=3.84 Hz), 8.81($H_6'$, doublet, J=0.93 Hz), 8.17 ($H_4'$, doublet, J=7.29 Hz), 7.77($H_5'$, doublet, J=5.5 Hz), 7.64($H_{9,13}$, doublet, J=8.8 Hz), 7.19($H_7$, singlet), 7.09($H_{10,12}$, doublet, J=8.61 Hz), 4.00 (isopropoxy-C2, triplet, J=8.3 Hz), 3.80($H_6$, triplet, J=5.64 Hz), 2.96 ($H_4$, triplet, J=12.03 Hz), 2.07($H_5$, triplet. J=9.4 Hz), 1.45(propoxy-C2,3, doublet, J=12.52 Hz).

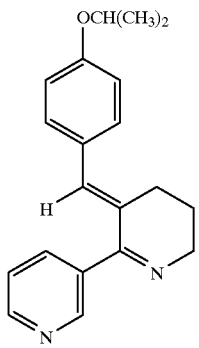

3-(4-isopropoxybenzylidene)anabaseine dihydrochloride ("GTS-85")

5.3 Example 3—Preparation of New Cinnamylidene Derivatives of Anabaseine

Preparation of trans-3-(4-Acetoxycinnamylidene) anabaseine Dihydrobromide by Condensation of trans-4-Acetoaxycinnamaldehyde with Anabaseine Dihydrobromide.

5.3.1 trans-4-Acetoxycinnamic Acid

A mixture of 3.28g (20 mmol) of 4-hydroxycinnamic acid in 10 mL of dry pyridine and 5 ml (53 mmol) of acetic acid anhydride was heated at reflux for 20 min. The yellow solution was poured onto ice/2N HCl (50/50) and stirred for 10 min. The resultant solid was filtered, washed with water and dried in air. Recrystallization of the crude material from acetone gave 2.14 g (10.4 mmol, 51%), of a white solid having a melting point of 210° C.

5.3.2 trans-4-Acetoxycinnamic Acid Chloride

To 4-acetoxycinnamic acid (2.00 g, 10.5 mmol) suspended in 40 mL of benzene and 2.00 g (16.8 mmol) of thionyl chloride was added 10 drops of N,N-dimethylformamide. After the suspension was heated at reflux for 2 hours, the yellow solution was concentrated under reduced pressure and the resultant greenish solid was taken up in benzene. The solution was filtered to remove insoluble material. Removal of the solvent and drying in vacuo gave 2.00 g (8.89 mmol, 85%) of the off-white acid chloride that was used in the next step without further purification.

5.3.3 trans-4-Acetoxycinnamaldehyde

To a stirred solution of 2.00 g (9.62 mmol) of 4-acetoxycinnamic acid chloride in 20 mL of dry THF at −65° C. was added 10 mL of lithium tri-t-butoxyaluminohydride (1N in THF) over a period 15 minutes. After the addition was complete, the heterologous reaction mixture was stirred for 1 hour at this temperature. The cooling bath was then removed and the reaction mixture was allowed to warm to room temperature to give a clear yellow solution. The reaction was quenched by adding 50 mL of 1 N HCl and 60 mL of ether. The organic layer was separated and the aqueous phase was extracted with ether (30 mL). The combined organic phase was washed with water (50 mL) and an aqueous solution of saturated $NaHCO_3$ (50 mL) and then dried over $Na_2SO_4$. Removal of the solvent gave 1.43 g of a greenish oil, which was purified by chromatography on silica using hexanes/ethyl acetate (70/30) to give 910 mg (4.79 mmol, 50%) of the off-white 4-acetoxycinnamaldehyde, having a melting point of 77–80° C. The compound was dissolved in dichloromethane before it was applied to the column. Also collected was 460 mg of a yellowish byproduct, that was identified by $^1$H NMR (300 MHz, $CDCl_3$) as the corresponding alcohol.

5.3.4 Condensation of trans-4-Acetoxycinnamaldeyde with Anabaseine

Anabaseine dihydrobromide monohydrate (100 mg, 0.294 mmol) and 200 mg (1.05 mmol) of 4-acetoxycinnamaldehyde were dissolved in 5 ML of acetic acid containing 5 drop of acetic acid anhydride. The mixture was heated to 70° C. in a sealed tube for 24 hours and the resultant yellow solid was isolated by filtration, washed with ether and dried in vacuo at 100° C. $^1$H NMR revealed the presence of a small amount of aldehyde; therefore, the material was heated at reflux in acetic acid containing several drops of acetic acid anhydride. Drying in vacuo at 100° C. gave 86 mg (0.17 mmol, 59%) of an orange solid, having a melting point of >220° C. Elemental analysis for $C_{21}H_{22}Br_2N_2O_2$. Calculated: C, 51.04, H, 4.49, N, 5.67. Found: C, 50.97; H, 4.06; N, 5.21. $^1H$ NMR (DMSO-$d_6$): δ8.93 (1H, doublet, J=4 Hz), 8.84 (1H, singlet), 8.13 (1H, doublet, J=8 Hz), 7.74 (3H, multiplet), 7.50 (1H, multiplet), 7.33 (1H, doublet, J=11 Hz), 7.20 (2H, doublet, J=8 Hz), 7.00 (1H, doublet, J=11 Hz), 5.29 (broad), 3.80 (2H, triplet, J=6 Hz), 2.95 (2H, triplet, J=6 Hz), 2.28 (3H, singlet), 2.08 (2H, multiplet).

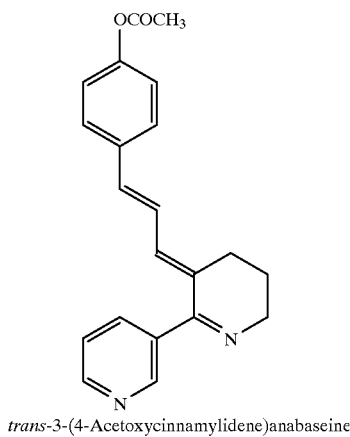

trans-3-(4-Acetoxycinnamylidene)anabaseine

5.4 Example 4—Preparation of trans-3-(4-Hydroxycinnamylidene)anabaseine Dihydrobromide Monohydrate by Condensation of trans 4-Hydroxycinnamaldehyde with Anabaseine.

5.4.1 trans-4-Hydroxycinnamaldehyde

To an ice-water cooled solution of trans-4-acetoxycinnamaldehyde (1.10 g, 5.78 mmol) in 25 mL of chloroform was added 250 mg of sodium metal dissolved in 5 mL of methanol. The yellow mixture was allowed to stand for 30 minutes at room temperature. 50 mL of 1 N $H_2SO_4$ was added to the reaction mixture and the organic layer was separated. The aqueous phase was extracted with chloroform (5×30 mL) and the combined organic phase was dried over $MgSO_4$. The solvent was then removed and the greenish solid was dissolved in ethyl acetate (40 mL), mixed with 5 g of silica and evaporated to dryness. The adsorbed material then was dissolved in solvent, applied to a silica column preconditioned with a mixture of ethyl acetate to hexanes (3 to 7), and eluted with mixtures of ethyl acetate and hexanes (30% increasing to 50% of ethyl acetate) to yield 710 mg (4.80 mmol, 82%) of a slightly yellow solid, melting point 135–137° C.

5.4.2 Condensation of trans-4-Hydroxycinnamaldehyde with Anabaseine

Anabaseine dihydrobromide monohydrate (100 mg, 0.294 mmol) and 100 mg (0.65 mmol) of 4-hydroxycinnamaldehyde dissolved in 5 mL of acetic acid was heated to 70° C. in a sealed tube for 24 hours. After the liquid was removed from the dark red crystals with a pasteur pipette, 3 mL of acetic acid was added and the solution was treated with ultrasound. The solid was filtered, washed with ether and dried in vacuo at 100° C. to yield 132 mg (0.280 mmol, 96%) of a dark red crystalline solid, having a melting point of >220° C. Elemental analysis for $C_{19}H_{20}Br_2N_2O \cdot H_2O$. Calculated: C, 48.53; H, 4.72; N, 5.96. Found: C, 48.90; H, 4.40; N, 5.94. HNMR (DMSO-$d_6$): δ 8.92 (1H, doublet, J=5 Hz), 8.83 (1H, singlet), 8.11 (1H, doublet, J=7 Hz), 7.75 (1H, doublet of doublets, J=5 Hz and 7.5 Hz), 7.59 (2H, doublet, J=8 Hz) 7.29 (2H, multiplet), 6.98 (1H, doublet, J=10 Hz), 6.82, (2H, doublet, J=8 Hz), 5.9 (broad), 3.77 (2H, multiplet), 2.90 (2H, multiplet), 2.05 (2H, multiplet).

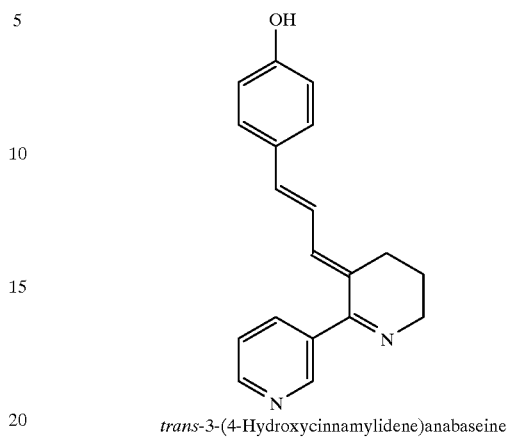

trans-3-(4-Hydroxycinnamylidene)anabaseine

5.5 Example 5–Preparation of trans-3-(4-Acetylaminocinnamylidene)anabaseine by Condensation of trans-4-Acetylaminocinnamaldehyde with Anabaseine Dihydrobromide.

5.5.1 trans-4-Acetylaminocinnamaldehyde

A solution of 0.8 mL (0.63 g, 14 mmol) of acetaldehyde in 40 mL of ethanol was added dropwise over 25 minutes to an ice-cold solution of 2.0 g (12 mmol) of 4-acetylaminobenzaldehyde in 60 mL of ethanolic KOH (2%). Stirring was continued at this temperature for 3 hours. The mixture was then neutralized with concentrated HCl and the solvent was evaporated under reduced pressure. The residue was purified by chromatography on silica with an elution solvent of 1:1 ethyl acetate:hexane. The recovered material was recrystallized from toluene to give 325 mg (1.72 mmol, 12%) of a yellow solid, melting range 167–173° C. The $^1H$ NMR spectrum showed the presence of an impurity (15%), probably the corresponding cis- isomer.

5.5.2 Condensation of trans-4-acetylaminocinnamaldehyde with Anabaseine

Anabaseine dihydrobromide monohydrate (100 mg, 0.294 mmol) and 100 mg (0.53 mmol) of 4-acetylaminocinnamaldehyde dissolved in 5 mL of acetic acid containing 5 drops of acetic acid anhydride was heated to 70° C. in a sealed tube for 24 hours. The black reaction mixture was diluted with 20 mL of ether. The precipitate was isolated by centrifugation and washed with acetic acid (5 mL) and ether (3×10 mL). The reddish solid was dissolved in 30 mL of $H_2O$, made basic using 20 mL of 10% aqueous $Na_2CO_3$ and extracted with dichloromethane (4×25 mL). The combined organic phase was dried over $Na_2CO_3$ and the solvent was removed in vacuo. The yellow oil (about 150 mg) was purified by chromatography on activity II alumina using freshly distilled acetone. Activity II alumina was made from 20 g of basic alumina (activity 1) by treating it with 0.8 mL of $H_2O$; the suspension was shaken for 10 minutes and allowed to stand in a closed container for 30 minutes prior to use. The yellow fractions were pooled and concentrated in vacuo to give a yellow-orange oil, which crystallized on stirring in ether. The base was isolated by filtration and dried at 100° C. in vacuo to give 66 mg (0.20 mmol, 67%) of an orange solid having an uncorrected melting point of 199–202. Elemental analysis for C21H21N3O ¼$H_2O$. Calculated: C, 75.08; H, 6.45; N, 12.5 1. Found: C, 75.5 1; H, 6.43; N, 12.29. $^1H$ NMR (CDCl$_3$): δ 8.69 (1H, singlet), 8.63 (1H, doublet, J=4 Hz), 7.78 (1H, doublet, J=8 Hz), 7.51 (2H, multiplet), 7.34 (3H, multiplet), 7.01 (1H doublet of doublet, J=11Hz and 15 Hz), 6.56 (1H, J=15 Hz), 6.33 (1H, J=11 Hz), 3.87 (2H, triplet, J=5 Hz), 2.75 (2H, triplet, J=5 Hz), 2.18 (3H, singlet), 1.89 (2H, multiplet).

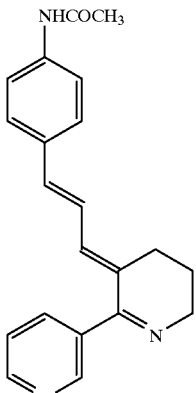

trans-3-(4-Acetylaminocinnamylidene)anabaseine 5.6 Example 6—Preparation of trans-3-(Cinnamylidene) anabaseine Dihydrochloride To a solution of anabaseine dihydrochloride (180 mg, 0.770 mmol), trans-cinnamaldehyde (0.25 mL, 1.9 mmol) and ethanol (20 mL) was added aqueous concentrated HCl (8 drops). The solution was heated at reflux for 4 hours. The reaction mixture was cooled to 0° C. and then diethyl ether was added dropwise until no more precipitate appeared (ca. 10–20 mL). The product was filtered off to give after drying 200 mg of a fine yellow powder which was recrystallized by dissolving it in warm isopropyl alcohol and precipitating it with ether. The result was 180 mg of a yellow solid (melting point 210–213° C., decomposed, 68% yield). $^1$H NMR (DMSO-$d_6$): δ 8.93 (H6', 1H, doublet, J=5 Hz), 8.86 (H2', 1H, singlet), 8.17 (H4', 1H, doublet, J=9 Hz,), 7.77 (H5', 1 H doublet of doublets), 7.70 (H2, H6, 2H, multiplet), 7.52 (Hβ, 1H, doublet of doublets, J=13 Hz and J=17 Hz), 7.40 (H3, H4, H5, 3H, multiplet), 7.29 (Hα, 1H, doublet, J=17 Hz), 6.98 (Hγ, 1H, doublet, J=12 Hz), 5.4 (N—H, 2H, broad), 3.78 (CH$_2$, 2H, multiplet), 2.93 (CH$_2$, 2H, multiplet), 2.04 ppm (CH$_2$, 2H, multiplet). Elemental analysis for $C_{19}H_{20}N_2Cl_2$. Calculated: C, 65.70; H, 5.80; N, 8.07. Found: C, 65.69, H, 5.85, N, 7.98.

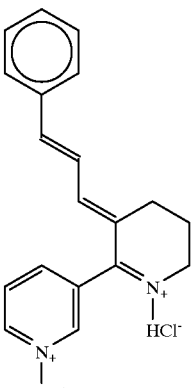

trans-3-(Cinnamylidene)anabaseine 5.7 Example 7—Preparation of trans-3-(2-Methoxycinnamylidene) anabaseine Dihydrochloride.

To a solution of anabaseine dihydrochloride (200 mg, 0.86 mmol), Trans-2-methoxycinnamaldehyde (348 mg, 2.10 mmol) and 20 mL of ethanol was added concentrated HCl (8 drops). The solution was heated at reflux for 4 hours while stirring. The reaction mixture was then cooled to 0° C. and the product was precipitated with diethyl ether (ca. 10–20 mL). The product was collected by filtration to give 220 mg of a yellow solid. The solid was recrystallized by dissolving it in warm isopropyl alcohol and precipitating it with diethyl ether to yield 200 mg of an orange solid (melting point 212–213° C., decomposed, 62% yield). A portion was converted to the free base by using saturated aqueous NaHCO$_3$ and extracting the product into ethyl acetate; a yellow solid then was collected. $^1$H NMR of the free base (CDCl$_3$): δ 8.63 (H2', 1H, doublet, J=2 Hz), 8.57 (H6', 1H, doublet of doublets, J=2 Hz and 6 Hz), 7.70 (H4', 1H, doublet of triplets, J=2 Hz, 2 Hz and 9 Hz), 7.42 (H6, 1H, doublet of doublets, J=2 Hz and 8 Hz), 7.27 (H5', 1H, doublet of doublets, J=2 Hz, 6 Hz and 9 Hz), 7.17 (H4, 1H, doublet of triplets, J=2 Hz, 8 Hz and 8 Hz), 7.05 (Hβ, 1H, doublet of doublet, J=12 Hz and 17 Hz), 6.90 (Hα, 1H, doublet, J=17 Hz), 6.85 (H5, 1H, triplet, J=8 Hz and 8 Hz), 6.78 (H3, 1H, doublet, J=8 Hz), 6.32 (Hγ, 1H, doublet, J=12 Hz), 3.80 (CH$_2$, 2H, multiplet), 3.78 (CH$_3$O, 3H, singlet), 2.68 (CH$_2$, 2H, multiplet), 1.80 ppm (CH$_2$, 2H, multiplet). Elemental analysis for $C_{20}H_{22}N_2Cl_2O·H_2O$ Calculated: C, 60.76, H, 6.12, N, 7.08. Found: C, 60.54, H, 6.03, N, 6.76.

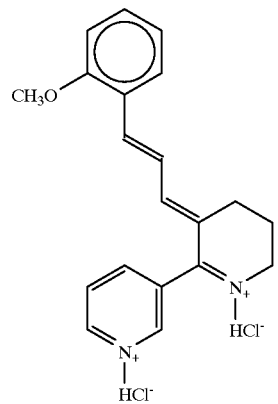

trans-3-(2-Methoxycinnamylidene)anabaseine 5.8 Example 8—Preparation of trans-3-(4-Methoxycinnamylidene) anabaseine Dihydrochloride.

To a solution of anabaseine dihydrochloride (400 mg, 1.70 mmol) and trans-4-methoxycinnamaldehyde (696 mg, 4.30 mmol) in 20 mL of ethanol was added concentrated HCl (16 drops). The solution was heated at reflux for 4 hours while stirring. The reaction mixture was cooled to 0° C. and the product was precipitated with diethyl ether (ca. 20–40 mL). The product was collected by filtration to give 410 mg of a yellow solid. The solid was recrystallized by dissolving it in warm isopropyl alcohol and precipitating it with diethyl ether to yield 350 mg of an orange solid (melting point 217–219° C., decomposed, 54% yield). $^1$H NMR (dihydrochloride, DMSO-$d_6$): δ 8.98 (H6', 1H, doublet, J=6 Hz), 8.94 (H2', 1H, singlet), 8.32 (H4', 1H, doublet, J=9 Hz), 8.78 (H5', 1H, doublet of doublets, J=9 Hz and 6 Hz), 7.66 (H2, H6, 2H, doublet, J=10 Hz), 7.38 (Hβ, 1H, doublet of doublets, J=17 Hz and 12 Hz), 7.24 (Hα, 1H, doublet, J=17 Hz), 6.95 (H3, H5 and Hγ, 3H, multiplet), 5.9 (N—H, 2H, broad), 3.76 (CH$_3$, 3H, singlet), 3.74 (CH$_2$, 2H, multiplet), 2.89 (CH$_2$, 2H, multiplet), 2.04 ppm (CH$_2$, 2H, multiplet). Elemental analysis for $C_{20}H_{22}N_2OCl_2$. Calculated: C, 63.67; H, 5.88; N, 7.43. Found: C, 63.32; H, 5.87; N, 7.32.

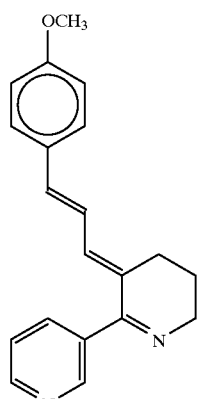

trans-3-(4-Methoxycinnamylidene)anabaseine 5.9 Example 9—Preparation of trans-3-(4-hydroxy-2-methoxycinnamylidene) anabaseine dihydrochloride ("GTS-86").

A mixture of 4-hydroxy-2-methoxycinnamaldehyde (178 mg, 0.93 mmol), anabaseine (150 mg, 0.63 mmol), 12 drops of concentrated HCl and 30 mL of absolute ethanol was refluxed for 4 hours. A yellow precipitate was obtained on adding 50 mL of ethylacetate. The product was washed with ethyl acetate to remove the unreacted 4-hydroxy-2-methoxycinnamaldehyde. Recrystallization from hot ethanol-ether gave the trans -3-(4-hydroxy-2-methoxycinnamylidene) anabaseine dihydrochloride (205 mg, 83%), $^1$H NMR (DMSO-d$_6$) : 8.98 (H$_2$', doublet, J=4.7 Hz), 8.89 (H$_6$', doublet, J=1.9 Hz), 8.14 (H$_4$', doublet, J=9.9 Hz), 7.74 (H$_5$', doublet of doublets, J=5.2 Hz and 4.7 Hz), 7.54 (H$_4$', doublet, J=9.9 Hz), 7.74 (H$_5$', doublet of doublets, J=5.2 Hz and 4.7 Hz), 7.54 (H$_{15}$, doublet, J=8.8 Hz), 6.82–7.34 (H$_{7,8,9}$, multiplet), 6.57(H$_{14,}$ doublet, J=10.8 Hz), 6.49(H$_{12}$, doublet, J=2.3 Hz), 3.76(H$_6$, triplet, J=7.4 Hz), 3.63(OMe, singlet), 2.71 (H$_4$, triplet, J=5.9 Hz), 1.79 (H$_5$, triplet, J=7.4 Hz), 10.51(N$_1$H$^+$, broad), 12.70(N$_2$H$^+$, broad). MS (FAB) (M-2Cl)+321.

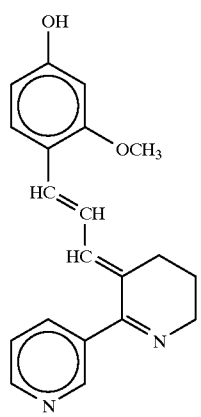

trans-3-(4-Hydroxy-2-methoxycinnamylidene)anabaseine 5.10 Example 10—Preparation of trans-3-(2,4-dimethoxycinnamylidene) anabaseine dihydrochloride ("GTS-87").

5.10.1 Acetaldehyde N-tert-butylimine

Acetaldehyde (8.8g, 0.2M) was added dropwise and with stirring over 1 hour to tert-butylamine (14.6g, 0.2M) at 0° C. Anhydrous potassium carbonate (3.0g) was added to the reaction mixture and stirred for 6 hours, and then decanted on to barium oxide (2.4g). After the mixture was stirred for 5 hours, it was filtered and the organic filtrate was distilled to separate the imine as a colorless liquid at reduced pressure (yield 80%).

5.10.2 2,4-Dimethoxycinnamaldehyde

To a cooled solution (−78° C.) of lithium diisopropylamide in 8 mL of tetrahydrofuran was added acetaldehyde N-tert-butylimine (0.4 mL, 3.0 mmol) and the mixture was stirred for 30 minutes. Diethyl chlorophosphate (518 mg, 3.0 mmol) was added and the solution was stirred at −78° C. for 2 hours, allowed to warm to −10° C. over a period of 3 hours, and recooled to −78° C. 2,4-dimethoxybenzaldehyde (232 mg, 2.0 mmol) was added to the yellow solution and the mixture was stirred for 30 minutes and allowed to warm to ambient temperature overnight. The mixture was then treated with oxalic acid (6 mmol in 20 mL of water) and then 20 mL of benzene was added. The two phase system was stirred overnight at room temperature and the layers separated. The aqueous layer was extracted with ether and the organic layers were combined and washed successively with 5% oxalic acid, 15% sodium bicarbonate, and brine. Drying (potassium carbonate) and concentration of the organic phase followed by purification of the residue (distillation or preparative TLC, silica gel, 30 ethyl acetate-hexane) gave 261 mg of 2,4-dimethoxycinnamaldehyde (yield 68%).

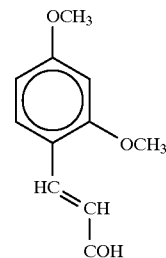

2,4-Dimethoxycinnamaldehyde 5.10.3 trans-3-(2,4-dimethoxycinnamylidene)anabaseine dihydrochloride ("GTS-87")

A mixture of 2,4-dimethoxycinnamaldehyde (230 mg, 1.2 mmol), anabaseine (233 mg, 1 mmol), 4 drops of concentrated HCl and 5 mL of absolute ethanol was refluxed for 6 hours. A yellow precipitate was obtained on adding 50 mL of ethyl acetate. The product was washed with ethyl acetate to remove the unreacted 2,4dimethoxycinnamaldehyde. Recrystallization from hot ethanol-ether gave the trans-3(2,4-dimethoxycinnamylidene)anabaseine dihydrochloride (317 mg, 78% yield). $^1$H NMR (DMSO-d$_6$): 8.89(H$^{2'}$, doublet, J=4.5 Hz), 8.79 (H$_6$', doublet, J=2.0 Hz), 8.18 (H$_4$', doublet, J=9.0 Hz), 7.64 (H$_5$', doublet of doublets, J=5.2 Hz and 4.7 Hz), 7.42 (H$_{15}$, doublet, J=8.8 Hz), 6.72–7.44(H$_{7,8,9}$, multiplet), 6.65(H$_{14}$, doublet, J=10.1 Hz), 6.52(H$_{12}$, doublet, J=2.1 Hz), 3.79(H$_6$, triplet, J=7.1 Hz), 3.65(OMe, singlet), 2.75(H$_4$, triplet, J=5.9 Hz), 1.76 (H$_5$, triplet, J=7.4 Hz). MS(FAB) (M+H)+408.

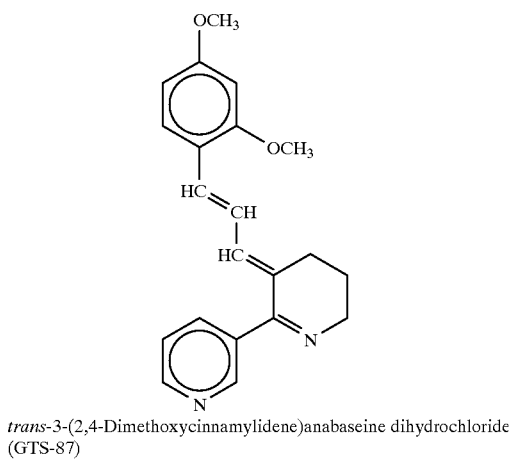

trans-3-(2,4-Dimethoxycinnamylidene)anabaseine dihydrochloride (GTS-87)

5.11 Example 11—Receptor Properties and Therapeutic Actions of Cinnamylidene-anabaseines Cinnamylidene-anabaseine compounds were found to displace high affinity alpha-bungarotoxin binding from rat brain membranes with higher affinity than would be predicted from studies with benzylidene-anabaseines (Table 2). Further, the cinnamylidene-anabaseines displaced high affinity cytisine binding to rat brain membranes with lower affinity than other types of benzylidene-anabaseines. These observations are consistent with the cinnamylidene-anabaseines having some selectivity for alpha7 receptor subtypes over other types of nicotinic receptors, especially alpha4beta2 receptors, based on the types of receptors to which alpha-bungarotoxin and cytisine bind to in brain.

The ability of cinnamylidene-anabaseines to act as agonists at alpha7 receptors but not at alpha4beta2 receptors was demonstrated in Xenopus oocytes. Each cinnamylidene-anabaseine studied elicited significant or complete activation of alpha7 receptors compared to the endogenous transmitter acetylcholine (Table 2). In contrast, none of these agents elicited significant activation of alpha4beta2 receptors (Table 2). These agents also antagonized the alpha7 receptor and alpha4beta2 receptor, the former observation occurring after receptor-activation. Blockade of the alpha4beta2 receptor, though observed at higher concentrations than alpha7 activation, may be important for therapeutic activity as well, as described below. In addition, the cinnamylidene-anabaseines are the first class of compounds known to have full agonist efficacy and high agonist potency at alpha7 receptors, which provide a degree of potential therapeutic benefit not observed with partial agonists.

E,E-3-(Cinnamylidene) anabaseine(3-CA), E,E-3-(2-methoxycinnamylidene) anabaseine(2-MeOCA), and E,E-3-(4-methoxycinnamylidene) anabaseine (4-MeOCA) displaced [$^{125}$I]α-bungarotoxin binding from rat brain membranes and activated rat α7 receptors in an oocyte expression system fully efficaciously. The potency series for binding and receptor-activation was 2-MeOCA>4-MeOCA=3-CA and 2-MeOCA=3-CA>4-MeOCA, respectively. No compound activated oocyte-expressed α4β2 receptors. While each cinnamylidene-anabaseine caused a long term inhibition of α7 receptors, as measured by ACh-application 5 min later, this inhibition ranged considerably, from under 20% (3-CA) to 90% (2-MeOCA) at identical 10 $\mu$M concentrations. These compounds improved passive avoidance behavior in nucleus basalis lesioned rats, with 2-MeOCA most potent in this respect. In contrast, only 3-CA was neuroprotective against neurite-loss during NGF-deprivation in differentiated PC12 cells. Choline, an efficacious α7 agonist without antagonist activity, was also protective in this model. These results suggest that the neurite-protective action of α7 receptor agonists may be more sensitive to potential long term antagonist properties than acute behavioral actions.

The alpha7 selective actions of these drugs is expected to give them a variety of activities of therapeutic value, including: 1) memory dysfunction associated with Alzheimer's disease and other disorders associated with learning and memory deficits; 2) brain cell loss associated with stroke, ischemia, or Alzheimer's disease; 3) treating alcohol withdrawal and intoxication; and 4) cigarette-withdrawal. Support for using alpha7 receptors agonists for each of these indications is indicated in the following experiments.

Several analogs of DMAC were synthesized with the 3-cinnamylidene anabaseine structure containing either no substituent-group or a methoxy-group at the 2- or 4-position. These were characterized relative to α7 receptor binding in rat brain tissue, α7 receptor activity (agonist and antagonist) in an oocyte expression system, improvement in passive avoidance behavior in nucleus basalis lesioned rats, and neurite-protection in NGF-deprived, differentiated PC12 cells. Choline was also investigated with respect to its neuroprotective activity as a prototypical α7-selective agonist with no antagonistic activity.

5.11.1 Cinnamylidene synthesis
Preparation of E,E-3-(cinnarnylidene)anabaseines.

All chemicals were purchased from Aldrich Chemical Company, Inc., Cinnamylidene-anabaseines were synthesized and characterized as follows: E,E-3-(Cinnamylidene) anabaseine dihydrochloride: To a solution of anabaseine dihydrochloride1 (180 mg, 0.772 mmoles), trans-cinnamaldehyde (0.25 mL, 1.9 mmol) and ethanol (20 mL) was added aqueous concentrated HCl (8 drops). The solution was heated at reflux for 4 hours. The reaction mixture was cooled to 0° C. and then diethyl ether was added dropwise until no additional precipitate appeared (ca. 10–20 mL). The product was filtered to give after drying 200 mg of a fine yellow powder which was recrystallized by dissolving it in warm isopropyl alcohol and precipitating it with ether. The result was 180 mg (0.519 mmol) of a yellow solid (mp 210–213° C. decomp., 67% yield). $^1$H NMR (DMSO-d$_6$):δ 8.93 (H6', d, 5 Hz, 1H), 8.86 (H2', s, 1H), 8.17 (H4', d, 9 Hz, 1H), 7.77 (H5', dd, 1H), 7.70 (H2, H6, m, 2H), 7.52 (Hβ, dd, 13 and 17 Hz, 1H), 7.40 (H3, H4, H5, m, 3H), 7.29 (Hα, d, 17 Hz, 1H), 6.98 (Hγ, d, 12 Hz, 1H), 5.4 (N—H, b, 2H), 3.78 (CH$_2$, m, 2H), 2.93 (CH$_2$, m, 2H), 2.04 ppm (CH$_2$, m, 2H). Anal. Calcd. for C$_{19}$H$_{20}$N$_2$Cl$_2$: C, 65.70; H, 5.80; N, 8.07. Found: C, 65.69, H, 5.85, N, 7.98.

E,E-3-(2-Methoxycinnamylidene)anabaseine dihydrochloride:

To a solution of anabaseine dihydrochloride (200 mg, 0.858 mmol), trans 2methoxycinnamaldehyde (348 mg, 2.10 mmol) and 20 mL of ethanol was added concentrated HCl (8 drops). The solution was heated at reflux for 4 hours while stirring. The reaction mixture was cooled to 0° C. and the product was precipitated with diethyl ether (ca. 10–20 mL). The product was collected by filtration to give 220 mg of a yellow solid. The solid was recrystallized by dissolving it in warm isopropyl alcohol and precipitating it with diethyl ether to yield 200 mg (0.506 mmol) of an orange solid (mp 212–213° C. decomp., 59% yield). A portion was converted to the free base by using sat. aqueous NaHCO$_3$ and extracting the product into ethyl acetate; a yellow solid then was collected. $^1$H NMR of the free base (CDCl$_3$): δ 8.63 (H2', d, 2 Hz, 1H), 8.57 (H6', dd, 2 and 6 Hz, 1H), 7.70 (H4', dr, 2, 2 and 9 Hz, 1H), 7.42 (H6, dd, 2 and 8 Hz, 1H), 7.27 (H5', ddd, 2, 6 and 9 Hz, 1H), 7.17 (H4, dr, 2, 8 and 8 Hz, 1H), 7.05 (Hβ, dd, 12 and 17 Hz, 1H), 6.90 (Hα, d, 17 Hz, 1H), 6.85 (H5, t, 8 and 8 Hz, 1H), 6.78 (H3, d, 8 Hz, 1H), 6.32 (Hγ, d, 12 Hz, 1H), 3.80 (CH$_2$, m, 2H), 3.78 (CH$_3$O, s, 3H), 2.68 (CH$_2$, m, 2H), 1.80 ppm (CH$_2$, m, 2H). Anal. Calcd. for C$_{20}$H$_{22}$N$_2$Cl$_2$O.H$_2$O: C, 60.76; H, 6.12, N, 7.08. Found: C, 60.54, H, 6.03, N, 6.76.

E,E-3-(4-Methoxycinnamylidene)anabaseine dihydrochloride:

To a solution of anabaseine dihydrochloride (400 mg, 1.72 mmol) of trans 4methoxycinnamaldehyde (696 mg, 4.30 mmol) and 20 mL of ethanol was added concentrated HCl (16 drops). The solution was heated at reflux for 4 hr while stirring. The reaction mixture was cooled to 0° C. and the product was precipitated with diethyl ether (ca. 20–40 mL). The product was collected by filtration to give 410 mg of a yellow solid. The solid was recrystallized by dissolving it in warm isopropyl alcohol and precipitating it with diethyl ether to yield 350 mg (0.928 mmol) of an orange solid (mp 217–219 0C, dec., 54% yield). $^1$H NMR (DMSO-d$_6$): δ 8.98 (H6', d, 6 Hz, 1H), 8.94 (H2', s, 1H), 8.32 (H4', d, 9 Hz, 1H), 8.78 (H5', dd, 9 and 6 Hz), 7.66 (H2,6 d, 10 Hz, 2H), 7.38 (Hβ, dd, 17 and 12 Hz), 7.24 (Hα, d, 17 Hz, 1H), 6.95 (H3,5 and Hγ, m, 3H), 5.9 (NH, b, 2H), 3.76 (CH$_3$, s, 3H), 3.74 (CH$_2$, m, 2H), 2.89 (CH$_2$, m, 2H), 2.04 ppm (CH$_2$, m, 2H) Anal. Calcd. for C$_{20}$H$_{22}$N$_2$OCl$_2$: C, 63.67; H, 5.88; N, 7.43. Found: C, 63.32; H, 5.87; N, 7.32.

5.11.2 Animals

Male Sprague Dawley albino rats (250–350 g) were purchased from Charles River Laboratories (Boston, Mass.) and maintained in the University of Florida Health Center Vivarium according to NIH guidelines, on a 12 hr:12 hr day:night cycle. They had ad libitum access to food (Purina rat chow) and water. Female Xenopus were housed in aquarium tanks maintained precisely at 18° C. to reduce potential problems with seasonal variability in oocyte viability. Frogs were fed frog brittle (Nasco) and kept on a 12 hr light:dark cycle.

5.11.3 Oocyte recordings

Oocytes were prepared and recordings made as described previously (de Fiebre, et al., 1995). Frogs were anesthetized by submersion in 0.1% (3)-aminobenzoic acid ethyl ester and several lobes of the ovary surgically removed through a small incision in the abdomen wall. Oocytes were freed from the follicle cells by treatment with collagenase (in calcium-free Barth's solution: 88 mM NaCl, 1 mM KCl, 15 mM Hepes pH 7.6, 0.33 mM MgSO$_4$, 0.1 mg/ml gentamicin sulfate) for 2 hr at room temperature and Stage 5 oocytes were isolated. Oocytes were rinsed and stored at 18° C. in Barth's saline (88 mM NaCl, 1 mM KCl, 15 mM Hepes pH 7.6, 0.3 mM Ca(NO$_3$)$_2$, 0.41 mM CaCl$_2$, 0.82 mM MgSO$_4$, 0.1 mg/ml gentamicin sulfate) before and after microinjection with RNA. Microinjection was conducted with a Drummond Scientific "Nanoject Variable" automatic injector. Oocytes were injected with a 50 nl solution of specified rat nicotinic subunit mRNA species (2–10 mg/ml; derived from the cDNA containing HIP 306 plasmid kindly provided by Dr. Jim Boulter, Salk Institute) and incubated 2–7 days at 18° C. before electrophysiological recording. electrophysiological recordings, oocytes were perfused in a Warner Instruments RC-8 recording chamber with a perfusion solution containing 115 mM NaCl, 2.5 mM KCl, 10 mM Hepes pH 7.2, 1.8 mM CaCl$_2$ and 1 μM atropine to block muscarinic responses. Perfusion was continuous at a rate of 10 ml/min. Drags were diluted in perfusion solution and applied using a solenoid valve to switch from perfusion to drug solutions. Current responses to drug administration were studied under two electrode voltage clamp at a holding potential of −70 mV using a Dagan Corp. TEV-200 voltage clamp connected to a 386-SX IBM computer using a TL-1 DMA interface (Axon Instruments). Micropipettes were filled with 3 M KCl and had resistances of 0.5–2 MOhms. Drug responses are analyzed with PClamp software (Axon Instruments). Oocytes with resting potentials of less than −30 mV were rejected.

5.11.3 High affinity [$^{125}$I]α-bungarotoxin binding

Rats were decapitated, and cerebral cortices were removed and homogenized in 10 vol of ice-cold Krebs-Ringer's Hepes (KRH) buffer (NaCl, 118 mM; KCl, 4.8 mM; MgSO4, 1.2 mM; CaCl$_2$, 2.5 mM; and Hepes, 20 mM; pH adjusted to 7.5 with NaOH), and then assayed for high affinity [$^{125}$I]α-bungarotoxin binding as described previously (18). Atropine (1 μM) and physostigrnine (10 μM) were added to prevent muscarinic receptor binding and ACh-hydrolysis, respectively. Binding assays were conducted at 4° C. in KRH buffer. The final incubation contained 500–800 μg protein/250 μl with 0.5 nM [$^{125}$I]α-bungarotoxin. Binding was terminated by diluting with 3 ml of ice-cold KRH buffer, followed immediately by filtration through glass fiber filters soaked in buffer containing 0.5% polyethylenimine. The filters were washed 4 times with 3 ml aliquots of ice-cold buffer. Nonspecific binding was determined with 100 μM unlabeled nicotine.

5.11.4 Neuroprotection Assay

PC12 cell-culture methods were modified from Greene and Tischler (1976). Cells were plated at 30–40% confluence and grown in Dulbecco's Modified Eagle Medium containing 10% heat-inactivated horse serum, 5% fetal bovine serum, 100 units/ml penicillin, 100 μg/ml streptomycin and 0.5 mM 1-glutamine. Cultures were maintained at 37° C., 94% O$_2$/6% CO$_2$ and 90–92% humidity in culture plates pre-coated with poly-1lysine (10 g/L). Cultures were maintained for 7 days in serum-supplemented medium to which 100 ng/ml rat 2.5S NGF was added at day 1. On day 7, conditioned medium was replaced serum-free medium containing specified drugs. Four days later, cell density was estimated using the NIH Image program version 1.47 and number of neurite-expressing cells counted manually in blind fashion as described previously (Martin et al., 1994). A Nikon inverted microscope (100× magnification) was attached to a Mac II computer via a monochrome video camera (Cohu, Inc., San Diego, Calif.). Four random areas were counted per plate and there were 4 plates per treatment group, unless otherwise indicated. Neurites were defined as processes at least 2× the length of the perikaryon. To assess the reliability of the image analyses, a reticle was used for direct quantification of cells in the same view as the one analyzed in random samples.

5.11.5 Passive Avoidance Behavior

Passive avoidance behavior was measured in nucleus basalis lesioned rats after intraperitoneal (IP) injections of drugs (base weight) or 0.9% saline diluent. For lesions, male 5 month old Sprague Dawley rats were anesthetized with 30 mg/kg sodium pentobarbital (IP) and then infused bilaterally with 1 μl of 5 μg/μl ibotenic acid in phosphate buffered saline, pH 7.4, into the nucleus basalis as described previously (17). Infusion coordinates were anterior 7.0 mm, lateral 2.6 mm and vertical 6.5 mm according to Paxinos and Watson (Paxinos and Watson, 1986).

Following surgery, animals were returned to their individual home cages and fed semi-solid mash made from Purina Rat Chow for several days. One month later, animals were trained in a two chamber passive avoidance paradigm.

Fifteen min after IP drug injection, they were placed in the lit compartment, and allowed to enter the dark adjoining chamber. Animals that entered the second chamber received a mild foot shock (0.8 mA) for 1 sec. Rats were tested for latency 24 hr later for up to 5 min; this test also began 15 min after injection. Statistical analyses utilized rank order non-parametric comparisons of latencies.

Histological assessments of the ibotenic acid placements in the nucleus basalis were made after behavioral measurements, using cholinesterase staining in formalin-fixed tissues. These injections typically reduced the number of cholinesterase-staining cells by over 80% in the nucleus basalis, with some loss of staining in the globus pallidus and thalamus as well, as determined with the NIH Image 1.47 program.

5.11.6 Results

Rat brain membranes bound to $[^{125}I]\alpha$-bungarotoxin in a 100 μM nicotine-displaceable manner with a Kd of 1.9 nM according to Scatchard analysis (r=0.98; single site model). Each 3-cinnamylidene anabaseine completely blocked high affinity, nicotine-displaceable $[^{125}I]\alpha$-bungarotoxin binding from rat brain membranes in a concentration-related manner (IC50 values: 3-CA, 80 nM; 4-MeOCA, 54 nM; 2-MeOCA, 8 nM) (FIG. 10).

ACh displayed typical agonist activity at α7 and α4β2 nicotinic receptors expressed in Xenopus oocytes (FIG. 11 AND FIG. 12). The cinnamylidene-anabaseine compounds were also efficacious with respect to activating rat α7 homo-oligomeric receptors, without activity at the α4β2 combination. 3-CA and 2-MeOCA had similar α7 $EC_{50}$ potency values (3.2±0.7 μM and 6.2±2.2 μM, respectively), while 4-MeOCA was 2–3 times less potent ($EC_{50}$=15.9±7.9 μM).

Antagonist properties subsequent to agonist activity were measured as a decrease in responsiveness to ACh applied 5 min after compound-application, normalized to ACh application instead of the anabaseine-derivative (FIG. 13A AND FIG. 13B). ACh administration had no long term inhibitory activity, as noted in previously. However, the cinnamylidene-anabaseines displayed concentration-dependent antagonist activity that varied in relative potency from what was observed with agonist activity. The $IC_{50}$ values for 3-CA, 2-MeOCA and 4-MeOCA were 15±6 μM, 2.3±0.7 μM, and 5.0±2.3 μM, respectively. There was no clear relationship between agonist- and antagonist-potencies for α7 receptors among these 3 compounds. None of the compounds elicited significant antagonism to α4β2 receptors up to concentrations of 30 μM (FIG. 14A AND FIG. 14B).

Bilaterally nucleus basalis-lesioned rats injected with saline diluent performed poorly in the passive avoidance paradigm compared to sham-operated controls (FIG. 2). The 3 cinnamylidene-anabaseines each improved passive avoidance behavior in the lesioned animals in an inverted U-shaped, dose-related manner when administered IP. 2MeOCA was the most potent performance-enhancing agent of this group. None of the agents altered performance during the training interval over the dose-ranges in which test-performance was improved, suggesting that there was no drug-induced change in locomotor function; higher doses did cause animals to be untrainable, with apparent loss of coordination without convulsions or unconsciousness.

Removal of NGF from differentiated PC12 cultures led to significant neurite loss 4 days later compared to plates in which NGF remained (FIG. 11). 3-CA protected against NGF-deprivation neurite loss at a 10 μM concentration, while the other two compounds had no effect. Choline also protected against NGF-withdrawal induced cell death at over 1–10 mM concentration range previously found to activate these receptors selectively in oocytes (FIG. X).

5.11.7 Discussion

Binding and physiological studies have indicated that the 3-cinnamylamine anabaseine structure is sufficient to confer high affinity and agonist-potency for rat α7 receptors. The simplest 3-cinnamylamine anabaseine, 3-CA, was potent and efficacious, and also expressed relatively little antagonist activity. Addition of a methoxy group to either the 2⁻or 4⁻position conferred significant additional properties at the α7 receptor. Addition of the methoxy group to the 2-position conferred the highest affinity for α7 of any compound yet reported in this class, while also increasing antagonist potency. The 4substituted cinnamylidene anabaseine (4-MeOCA) had agonist and antagonist receptor properties similar to those reported for DMAC, which is also a 4-substituted cinnamylidene-anabaseine (de Fiebre, et al., 1995): less affinity for the α7 receptor than the unsubstituted, but higher antagonist potency.

One of the long term difficulties in comparing the results of α7 binding studies to studies of receptor-function has been the much higher potency of agonists in the former type of system. This discrepancy is seen for cinnamyladine anabaseines as well, with displacement of α-bungarotoxin by each ligand observed at concentrations 10–100 less than those necessary to activate the receptor. Oocyte-expression studies yield agonist potencies similar to those observed in rat brain, so this phenomenon is not the result of an artifact in the oocyte-expression system. Instead, the rapid desensitization of the α7 receptor, which occurs before the peak agonist-concentration can be attained in the superfusion system, and appears to be at least one underlying factor of the binding/potency difference.

While the brain possesses many nicotinic receptor subtypes, the two predominant ones appear to consist of α4β2 and α7 subunits, based on binding and immunological studies. All of the 3-cinnamylidene anabaseines characterized to date (DMAC, 3-CA, 2-MeOCA, 4-MeOCA) selectively activate α7 receptors over α4β2, indicating at least some degree of nicotinic receptor selectivity. DMAC selectivity is observed over other nicotinic receptor subunit combinations as well (de Fiebre, et al., 1995). The 3-substituted benzylidene anabaseine DMXB is also selective as an agonist for α7 versus other nicotinic receptor subtypes (Meyer, et al., in press), although it has only weak partial agonist activity at these receptors compared to the cinnamylidene-substituted analogs in the present study.

Ibotenate-treated, nucleus basalis-lesioned rats offer a well studied model for memory-related dysfunction in passive avoidance behavior. α7 receptor activation is sufficient to improve this type of behavior, consistent with these receptors being localized in hippocampus and neocortex, areas associated with learning and behavior. The relative potencies of the 3 novel compounds in this behavioral paradigm are consistent with their receptor binding or activation. There was no relationship between this behavioral activity and antagonist activity. DMAC is also effective in this behavioral paradigm as (Meyer, et al., 1994) while possessing potent antagonist activity. It therefore appears that possessing antagonist activity does not interfere with this type of learning and memory related behavior.

NGF-deprivation in differentiated PC12 cells has been characterized extensively as a model of neuronal atrophy (Martin, et al, 1994). It has been demonstrated that α7 activation by GTS 21 is sufficient to reduce this neurotoxicity in this model (Martin, et al., 1994). The present results are consistent with this observation, since choline as well as 3-CA exhibited cytoprotective activity (FIG. ___). Choline has been shown to activate rat α7 receptors with a potency 10-fold lower than that of ACh, without effect at α4, α2, β2 or β4 containing subtypes (Papke, et al., 1996). The potency of choline at oocyte-expressed α7 receptors is therefore comparable to that observed for neuroprotection in the present assay.

Neither 2-MeOCA nor 4-MeOCA elicited neurite-protection at the same 10 μM concentration at which 3-CA was effective. This concentration was selected based on the results of oocyte studies because it permitted a comparison of the relative importance of agonist versus antagonist activity in neurite-protection, especially when comparing 3-CA to 2-MeOCA. Based on the oocyte receptor-expression results, it was estimated that 10 μM 3-CA and 2-MeOCA would activate similar fractions (over 75%) of α7 receptors, but would differentially inhibit α7 receptors: less than 20% inhibition for 3-CA and over 90% inhibition for 2-MeOCA. Based on this comparison, it appears that neuroprotective activity in the PC12 cell model is attenuated by α7 receptor antagonism when a similar level of receptor activation is present. This is consistent with the observation that choline has no antagonist activity at α7 receptors (Papke, et al., 1996). For 4-MeOCA it is difficult to resolve whether the lack of neurite protection may be due to low agonist potency or to significant antagonism, or both.

The apparent sensitivity of the neurite-protective activity to the antagonist properties of the α7 agents may derive from the long term nature of these studies. In contrast to behavioral studies that are conducted shortly after drug administration, the present neuroprotection studies take place over 4 days. Alternatively, it is possible that different mechanisms may be underlying the neuroprotective vs. behavioral action. The role of the α7 receptor in maintaining calcium homeostasis and intracellular transduction processes may be differentially sensitive to the antagonist-properties of α7 agonists than the acute changes in membrane potential, which may be sufficient to modulate behavior.

5.12 Example 12—Cinnamylidene-anabaseines to treat Alzheimer's disease and other pathological conditions interfering with learning and memory Nicotine improves learning and memory related behaviors in humans and animals. In Alzheimer's disease, for example, nicotine improves performance in several memory-related tasks, though the side effects associated with this disease were such that high doses could not be tolerated. Weak, albeit selective alpha7 receptor agonists with benzylidene-anabaseine structures improve learning and memory in a variety of animal models, including passive avoidance behavior, active avoidance behavior, and Morris Water task. These agents are effective only at rather high doses compared to nicotine, however, and their ability to only partially activate alpha7 receptors (in contrast with the full activation by the cinnamylidene-anabaseines described herein) may have been a factor in this observation as well as the observation that the range of effective doses for improving learning and memory related behaviors was not much greater than that of nicotine itself.

The disclosed alpha7 selective cinnamylidene-anabaseine compounds improved learning and memory behavior, using a passive avoidance paradigm and cholinergically hypofunctional rats that received nucleus basalis lesions comparable to cholinergic deficits in Alzheimer's disease (FIG. 2). The high potency of one of the cinnamylidene-anabaseines trans-3-(2-methoxycinnamylidene) anabaseine, along with its wider effective dose-response range (less than 0.1 mg/kg to at least 3 mg/kg) indicates that the cinnamylidene-anabaseines will have therapeutic advantages over benzylidene-anabaseines. In that the wider dose—response range indicates that patients may be dosed less often since there is a wider range of drug concentrations in brain that are behaviorally effective. The high potency indicates that low doses will be effective for improving memory related behaviors, which is generally associated with fewer side effects. trans-3(2-methoxy-cinnamylidene) anabaseine was less potent than the present compounds.

The alpha4beta2 receptor blocking actions of the disclosed cinnamylidenes-anabaseines may also be important for their therapeutic activity in learning and memory. Mice which have been genetically altered to have no alpha4beta2 receptors in their brains perform better in learning and memory tasks than normal animals. These results indicate that cinnamylidene-anabaseine compounds will have improved memory- and learning-enhancing effects compared to existing agents. A higher therapeutic index is expected due to a combination of full alpha7 efficacy and alpha4beta2 blockade.

5.13 Example 13—Cinnamylidene-anabaseines as neuroprotecting agents

Cinnamylidene-anabaseines were found to protect differentiated cholinergic PC12 neurons that were otherwise dependent on NGF for survival (Table 3). PC12 cells are known to possess both alpha7 and NGF receptors.* This neuronal survival model was found previously to be sensitive to drugs that stimulate protein kinase C activity or increased calcium-influx (Rukenstein, et al., 1991). Alpha7 receptors increase both calcium influx and protein kinase C activity when activated. These data suggested that cinnamylidene-anabaseines could replace the cytoprotective action of NGF in differentiated cells, and that these compounds would therefore be useful in conditions, such as Alzheimer's disease, for which NGF is currently thought to be a potential treatment.** Because this cytoprotective action may be mediated through a general phenomenon of receptor activation (calcium and protein kinase C activation (Rukenstein, et al., 1991), it is likely that related agents with alpha7 activation capacity will be similarly cytoprotective as well. Further, since nicotinic agents can protect against stroke-induced cell death, it is likely that these cinnamylidenes will be effective along these lines as well (e.g., FIG. 3).

\* The NGF—deprivation model shows apoptosis as evidenced by loss of neurites unless a neuro protective agent is added (Rukenstein, et al., 1991).
\*\* As contemplated by the inventors, the cinnamylidene anabaseines provided protection in the NGF-deprivation model when NGF was removed. Apoptosis may be involved in a variety of neuropathological conditions.

TABLE 2

Receptor-Characteristics of Cinnamylidene Compounds

| Compound | alpha7 binding[1] | alpha4beta2 binding[2] | alpha7 activation[3] | alpha4beta2 activation[4] | alpha 7 antagonism[5] | alpha4beta2 antagonism[6] |
|---|---|---|---|---|---|---|
| trans-3-cinnamylidene anabaseine | 94.7 | 6.2 | 92 | <3 | 45 | 10 |
| trans-3-(2-methoxy-cinnamylidene)anabaseine | 94.9 | 29 | 96 | <3 | 90 | 10 |
| trans-3-(4-methoxy-cinnamylidene)anabaseine | 94.1 | 32 | 45 | <2 | 75 | 34 |

[1] % inhibition of alpha-bungarotoxin binding at 1 $\mu$M concentration (higher number = higher affinity)
[2] % inhibition of cytistine binding at 1 $\mu$M concentration (higher number = higher affinity)
[3] % response observed with 500 $\mu$M acetylcholine (higher number = more agonist activity)
[4] % response observed with 10 $\mu$M acetylcholine (higher number = more agonist activity)
[5] % of antagonism of acetylcholine administered after drug (high number = more antagonism)
[6] % of antagonism of acetylcholine administered after drug (high number = more antagonism)

TABLE 3

Protection of NGF-Dependent PC12 Cells in Culture

| Compound | Neurite Counts |
|---|---|
| None | 83 ± 12 |
| NGF (100 ng/ml) | 342 ± 56* |
| trans-3-cinnamylidene-anabaseiene | 185 ± 19* |
| trans-3-(2-methoxycinnamylidene) anabaseine | 213 ± 26* |
| trans-3-(4-methoxycinnamylidene) anabaseine | 155 ± 23* |

PC12 cells were differentiated for 1 week with NGF. Drugs were administered for the 4 day interval after removal of serum and NGF. Neuites were counted and expressed as the mean±SEM of at least 3 plates/group. Drug concentrations (except NGF) were 10 $\mu$M. *p<0.05 compared to no drug treatment (one way ANOVA).

5.14 Example 14—Receptor Binding Properties of Benzylidene- and Cinnamylidene-Anabaseines

TABLE 4

| | Receptor Binding Oocytes | | | | | | | | | |
|---|---|---|---|---|---|---|---|---|---|---|
| Compound | Syn | Stab | α4 | α7 | α4 | α7 | Agonist Antagonist | PC12 Cyto. | PA Behav. | NB Lesion |
| GTS-21DMXB | ± | ± | 72 | 52 | <.01 | .20 | .20 | + | +++ | + |
| GTS-13 PABA 3-(4-amino-benzylidine)anabaseine | + | + | >90 | 93 | ? | .72 | .69 | + | +++ | ? |
| --Acetate--INSERT NAME | + | ? | 78.1 | 59.2 | ? | .50 | .46 | ? | ? | ? |
| GTS-2 3-(4-methoxy-benzylidene)anabaseine | + | + | >80 | — | ? | ? | ? | ? | ++ | |
| GTS-7 3-(4-hydroxy-benzylidene)anabaseine | + | + | >90 | 69.3 | ? | ? | ? | — | ± | |
| GTS-80 3-(2,4-dimethoxy-α-methyl-benzylidene) | + | + | 41 | 85 | ? | ? | ? | ? | ? | |
| GTS-62 3-(4-hydroxy-2-methoxybenzylidene) anabaseine | + | + | 87 | 84 | ? | .43 | .35 | ? | +(+) | |
| GTS-51 3-(2-hydroxy-4-methoxybenzylidene) anabaseine | + | + | >60 | | ? | .29 | .26 | — | ++(+) | |
| trans-3-(cinnamylidene)anabaseine | + | + | 6.2 | 94.7 | .026 | .92 | .50 | +? | ++ | |
| trans-3-(2-methoxycinnamylidene)anabaseine | + | + | 29.2 | 94.9 | .022 | .96 | .08 | — | ++++ | |
| trans-3-(4-methoxycinnamylidene)anabaseine | + | + | 31.8 | 94.1 | <0.05 | .45 | .104 | — | ++ | |
| GTS-82 or 86??trans-3-(4-hydroxy-2-methoxycinnamylidene)anabaseine | + | + | 53 | 90 | — | — | — | — | — | |
| GTS-87 trans-3-(2,4-dimethoxy-cinnamylidene)anabaseine | + | + | — | 76 | | | | | | |
| GTS-81 trans-3-(4-nitro-cinnamylidene) anabaseine | | | | | | | | | | |
| Antagonists | | | | | | | | | | |
| 15 3(4-dimethylaminopropoxy-benzylidene)anabaseine | + | + | 58 | 87 | ? | .03 | .02 | (?) | (?) | |

TABLE 4-continued

Receptor Binding Oocytes

| Compound | Syn | Stab | α4 | α7 | α4 | α7 | Agonist Antagonist | PC12 Cyto. | PA Behav. | NB Lesion |
|---|---|---|---|---|---|---|---|---|---|---|
| Reduced GTS-3(4-dimethoxy-benzylidene)anabasine | + | + | 50 | 9 | ? | ? | ? | | + | — |

(+) = In Between or Unknown
± = Not Yet Active
+ = ≧ 0.5
++ = 0.2
+++ = 0.1
++++ = <0.1

5.15 Example 15—Inhibition of Nicotine Self-Administration by Anabaseines

The most accepted animal test for demonstrating ability to block the nicotine reward is that of nicotine self-administration. The inventors have used this sophisticated technique to show that DMXB, a compound which acts as a nicotine antagonist at putative receptors mediating the nicotine reward, inhibits nicotine self-administration in the adult rat which has acquired the ability and motivation for nicotine ingestion. The advantage of this compound is that it accomplishes this without adversely affecting the animal's other functions, including its spontaneous locomotor activity.

Eleven male Sprague-Dawley rats were first trained to press the left lever in a two lever operant conditioning chamber. They had limited access to food for 23 hours prior to the first training session and then received 20 grams of food for the remainder of the study. Once subjects reliably pressed the left lever, a catheter was surgically implanted into the right jugular vein. The catheter consisted of three separate pieces of tubing, a 37 mm length of silicon rubber tubing which entered the circulatory system (Silastic Medical Grade tubing), a 65 mm length of polyethylene tubing (Intramedic, PE10) and a 170 mm length of polyethylene tubing with the same internal diameter (Intramedic, PE20). The catheter exited between the scapulae and could be hooked up to a swivel which itself was connected to a pneumatic syringe. Nicotine bitartrate (0.01 mg/kg of free base) could be delivered in a volume of 0.1 ml/kg over 0.75 seconds. Once subjects had recovered from surgery they were trained to complete a fixed ratio 2 schedule (FR 2) to activate the pneumatic syringe. A time-out (TO) period of 60 seconds, followed each administration of nicotine. Each daily experimental session lasted 50 minutes. After several sessions under these conditions, subjects received an intraperitoneal (IP) injection of physiological saline (1 ml/kg), 15 min prior to the start of the self-administration session. The next day subjects were IP injected with 8 mg/kg of GTS-21, also 15 minutes before the beginning of the session. FIG. 5 shows that subject were less likely to self-administer nicotine after GTS-21 than after saline administration (paired t(10)=2.48, p<0.05).

5.16 Example 16—DMXB Protection against NMDA triggered excitotoxicity

This example illustrates that α7 activation by DMXB protects against excitotoxicity triggered by N-methyl-D-aspartate (NMDA) receptor activation. NMDA receptors are highly permeant to calcium ions, but unlike desensitizing α7 nicotinic receptors, induce calcium-mediated excitotoxicity by remaining in an open state for extended intervals after activation.

Activation of α7 nicotinic receptors has previously been found to protect neurons against apoptotic degeneration caused by trophic factor deprivation. The inventors have shown that the selective α7 receptor agonist demethoxy benzylidene anabaseine (DMXB) also protects rat primary neocortical neurons against NMDA-receptor mediated excitotoxicity. Dose-related DMXB-induced neuroprotection was observed when administered 24 hr before, but not concomitantly, with excitatory amino acids. This was blocked by nicotinic but not muscarinic antagonist DMXB. Protection was observed primarily in penumbral areas and was blocked with the nicotinic antagonist mecamylamine, indicating that α7 receptor activation is neuroprotective.

5.16.1 Methods

Primary rat neocortical neuronal cultures

Neuron-enriched cultures were isolated from the rat cerebral cortex on embryonic days 16–18, and then cultured on plastic coverslips under conditions that killed dividing, non-neuronal cells (01). Only mature cultures (10–11 days post-plating) were employed. Neurotoxicity was induced with exposure to excitatory amino acids (EAA), for 10 min (glutamate or NMDA) or 60 min (kainate), followed by a 60 min EAA-free interval. Viable cells were determined by the Trypan blue exclusion procedure, and expressed as the fraction of total cells counted.

Focal ischemia model

Male Sprague Dawley albino male rats (250–300 g) were anesthetized with a subcutaneous injection of ketamine, xylazine, and acepromazine (3:3:1 mixture, 0.7 cc/kg). Atropine (0.4 mg/kg IP) was injected several min prior to dissection of the carotid artery from the vagus. The internal carotid artery (ICA) was dissected until its proximal bifurcation into the terminal ICA and pterygopalatine arteries were clearly defined. The pterygopalatine artery was clipped parallel to and flush with the terminal ICA. Another clip was applied to the common carotid artery (CCA). The distal aspect of the external carotid artery (ECA) was coagulated and a straight aneurysm clip was applied 4 mm distal to the proximal ICA bifurcation. A suture was passed through the arteriotomized ECA stump into the ICA until the tip was resting against the aneurysm clip. The suture was removed 30 min later, with body temperature maintained between 36.5–37.5° C. The ECA stump was coagulated with bipolar electrocautery. Clips were removed and the wound was irrigated with saline prior to suturing.

Rats were euthanised 24 hours post-infarction and their brains removed and sectioned coronally (2 mm). Sections were placed into a 2% solution of 2,3,5-triphyenyl-tetrazolium cholide (Sigma Chemical Co., St. Louis. Mo.) for 20 minutes at 37° C. The sections were removed to a petri dish and covered with 10% formaldehyde solution. The outline function of the NIH Image computer program (version 1.47) was used to estimate the infarcted and total brain areas for each section. Infarct size was calculated as percent of total brain area.

5.16.2 Results

Acute exposure to a 1 mM concentration of each EAA was sufficient to kill 50–60% of the neurons 1 hr later. DMXB protected against NMDA receptor-mediated toxicity in primary rat brain neuronal cultures in a concentration-dependent manner when administered 24 hr prior to either glutamate or NMDA (FIG. 6E). It had no effect on kainate-induced neurotoxicity, which is mediated by a non-NMDA receptor. The neuroprotective effect of DMXB was not observed when administered concomitantly with glutamate, in contrast to the blocking effect of the NMDA receptor antagonist MK-801 (FIG. 6F). DMXB did not interfere with high affinity [$^3$H]MK801 binding to rat brain membranes at concentrations up to 30 $\mu$M, arguing against a neuroprotective action via direct NMDA receptor blockade. These results indicate an indirect or noncompetitive attenuation of NMDA-induced excitotoxicity by DMXB.

DMXB-induced neuroprotection was sensitive to the non-selective nicotinic receptor antagonists hexamethonium, methyllycaconitine and mecamylamine, as well as the $\alpha$7-selective antagonist $\alpha$-bungarotoxin (FIG. 7). The nonselective agonist nicotine similarly protected against neuronal loss in a methyllycaconitine-sensitive manner, consistent with its previously reported action in this model (Akaike, et al., 1994).

The in vitro results prompted an investigation of the effects of DMXB-treatment on focal ischemia-induced infarct size following occlusion of the middle cerebral artery in vivo. Most of the damage was localized to the lateral caudate and neocortex, maximally 5 mm posterior to the frontal pole, which was used for statistical analyses (FIG. 8A, FIG. 8B). DMXB protected principally in the posterior infarct area, including portions of the lateral caudate nucleus and occipital cortex. These penumbral areas correspond to those protected by MK801 (Papke, 1993). The antagonist mecamylamine blocked this neuroprotective action of DMXB, corroborating nicotinic involvement. DMXB was ineffective when administered during the 30 mm ischemic insult, consistent with the lack of neuroprotection observed when it was administered concomitantly with glutamate in vitro. The need to activate $\alpha$7 receptors prior to NMDA-receptor activation in order to observe neuroprotection may account for the inability of endogenous acetylcholine to be neuroprotective when released during ischemic attacks.

These results indicate that the protective action of nicotine against NMDA-induced toxicity in primary neocortical neurons is mediated at least in part through the $\alpha$7 receptor subpopulation. $\alpha$7 receptor activation is sufficient to protect neurons in degeneration-models that are at least partially apoptotic in nature, such as differentiated PC12 cells after NGF-deprivation and septal cholinergic neurons after axotomy. In the sympathetic ganglion, choline also maintains neurons during NGF-deprivation through nicotinic receptor activation at concentrations which are selective for $\alpha$7 receptors (Steinbach and Ifune, 1989). The neuroprotective action of choline required receptor-mediated elevations in intracellular $Ca^{2+}$ levels, supporting the concept that $\alpha$7 receptor activation protects against trophic factor-deprivation through a $Ca^{2+}$ triggered mechanism.

Nicotine attenuates apoptosis in several non-neuronal cells through a protein kinase C (PKC)-dependent mechanism, and this calcium-sensitive enzyme appears to be activated by $\alpha$7 agonists in PC12 cells. Overall, these results suggest a model in which $\alpha$7-activation elevates intracellular calcium ion concentrations transiently, followed by PKC activation.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

6.0 REFERENCES

The following references, to the extent that they provide exemplary procedural or other details supplementary to those set forth herein, are specifically incorporated herein by reference.

Akaike, Tamura, Takeharu, Shimohama, Kimura, "Nicotine-induced protection of cultured cortical neurons against N-methyl-D-asparate receptor-mediated glutamate cytotoxicity," *Brain Res.,* 644:181–186, 1994.

Alkondon and Albuquerque, "Diversity of nicotinic acetylcholine receptors in rat hippocampal neurons. I. Pharmacological and functional evidence for distinct structural subtypes," *J. Pharmacol. Exp. Therap.,* 265:1455–1469, 1993.

Alkondon, Reinhardt, Lobron, Herrosen, Maelicke, Albuquerque, "Diversity of nicotinic acetylcholine receptors in rat hippocampal neurons. II. The rundown and inward rectifications of agonist-elicited whole-cell currents and identification of receptor subunits by in situ hybridization," *J. Pharmacol. Exp. Ther.,* 271:494–499, 1994.

Arneric, Sullivan, Briggs, Donnelly-Roberts, Anderson, Raszkiewicz, Hughes, Cadman, Adams, Garvey, et al., "(S)-3-methyl-5-(1-methyl-2-pyrrolidinyl) isoxazole (ABT 418): a novel cholinergic ligand with cognition enhancing and anxiolytic activities: I. In vitro characterization," *J. Pharmacol. Exp. Ther.,* 270:310–318, 1994.

Bederson, Pitts, Tsuji, Nishimura, Davis, Bartkowski, "Rat middle cerebral artery occlusion: Evaluation of the model and development of a neurological examination," *Stroke,* 17:472–479, 1986.

Blomquist, Ericson, Johnson, Engel, Soderpalm, "Voluntary ethanol intake in the rat: effects of nicotinic acetylcholine receptor blockade or subchronic nitotine treatment," *Eur. J Pharmacol.,* 314:257–267, 1996.

Burton and Tiffany, "The effect of alcohol consumption on craving to smoke," *Addiction,* 92:15–26, 1997.

Choi, "Calcium-mediated neurotoxicity: relationship to specific channel types and role in ischemic damage," *Trends Neurosci.,* 11: 465–469, 1988.

Clarke, Schwartz, Paul, Pert, Pert, "Nicotinic binding in rat brain: autoradiographic comparison of [$^3$H]acetylcholine, [3H] nicotine, and [$^{125}$H]-$\alpha$-bungarotoxin," *J. Neurosci.,* 5:1307–1315, 1985.

Collins, Wilkins, Slobe, Cao, Bullock, "Long-term ethanol and nicotine treatment elicit tolerance to ethanol," *Alcohol Clin. Exp. Res.* 20:990–999, 1996.

Colquhoun, Ogden, Mathie, "The nicotinic acetylcholine receptor: molecular architecture of a ligand-regulated ion channel," *Trends Pharmacol. Sci.,* 8:465–472, 1987.

Connor, Langlais, and Thal, "Behavioral impairments after lesions of the nucleus basalis by ibotenic acid and quisqualic acid," Brain Res., 555:84–90; 1991.

Couturier, Bertrand, Matter, Hemandez, Bertrand, Miller, Soledad. V., Barkas, T. and Ballivet, M.: A neuronal nicotinic acetylcholine receptor subunit ($\alpha$-7) is developmentally regulated and forms a homo-oligomeric channel blocked by abungarotoxin," Neuron, 5:8476–856, 1990.

Couturier, Bertrand, Matter, Hernandez, Bertrand, Miller, Soledad, Barkas, Ballivet, "A neuronal nicotinic acetylcholine receptor subunit ($\alpha$7) is developmentally regulated and forms a homo-oligomeric channel blocked by $\alpha$-BTX," Neuron, 5:846–856, 1990.

de Fiebre and Collins, "Classical genetic analyses of responses to nicotine and ethanol in crosses derived from long-and short-sleep mice," J. Pharmacol Exp. Ther., 261:173–180, 1992.

de Fiebre, Meyer, Kem and Papke, "Characterization of a family of anabaseine-derived compounds reveals that the 3-(4)-dimethylamino-cinnamylideine derivative is a selective agonist at neuronal nicotinic $\alpha$7/$\alpha$-bungarotoxin receptor subtypes," Mol. Pharmacol., 47:164–171, 1995.

Decker, Brioni, Sullivan, Buckley, Radek, Raszkiewicz, Kang, Kim, Giardina, Wasicak, et al., "(S)-3-methyl-5-(1-methyl-2-pyrrolidinyl) isoxazole (ABT 418): a novel cholinergic ligand with cognition enhancing and anxiolytic activities," J. Pharmacol. Exp. Ther., 270:319–328, 1994.

Dekker, Gage and Thai, "Delayed treatment with nerve growth factor improves acquisition of a spatial task in rats with lesions of the nucleus basalis magnocellularis: evaluation of the involvement of different neurotransmitter systems," Neuroscience 48:111–119, 1992.

Deneris, Connolly, Rogers and Duvoisin, "Pharmacological and functional diversity of neuronal nicotinic acetylcholine receptors," TIPS 12:34–40, 1991. 10. Dixon and Massey, Introduction to Statistical Analyses, McGraw-Hill Book Co., New York, 1969.

Deneris, Connolly, Rogers, Duvoisin, "Pharmacological and functional diversity of neuronal nicotinic acetylchonline receptors," TIPS, 12:34–40, 1991.

Flores, Rogers, Pabreza, Wolfe and Kellar, "A subtype of nicotinic cholinergic receptor in rat brain is composed of $\alpha$4 and $\beta$2 subunits and is up-regulated by chronic nicotine treatment," Molec. Pharmacol., 41:31–37, 1992.

Henningfield and Goldberg, "Stimulus properties of nicotine in animals and human volunteers: a review," In: Behavioral Pharmacology: the Current Status, Seiden and Balster, eds., pp. 433–449, Alan R. Liss, New York, 1984.

Hunter, Papke, de Fiebre and Meyer, "Facilitation of hippocampal LTP by an apparent $\alpha$7 nicotinic agonist," Neurosci. Lett., 168:130–134, 1994. 14. Hunter, Zornetzer, Jarvik and McGaugh, "Modulation of learning and memory: effects of drugs influencing neurotransmitters," In: Drugs, Neurotransmitters, and Behavior, Handbook of Psychopharmacology, Vol. 8, Iversen et al., eds., pp 531–577, Plenum Press, New York, 1977.

Koike, Martin, Johnson, "Role of $Ca^{2+}$ channels in the ability of membrane alepolarization to prevent neuronal death induced by trophic-factor deprivation: Evidence that levels of internal $Ca^{2+}$ determine nerve growth factor dependence of sympathetic ganglion cells., Proc. Natl. Acad. Sci. USA, 86:6421–6425, 1989.

Marks et al., 1989.

Marks, Stitzel, Romm, Wehner and Collins, "Nicotinic binding sites in rat and mouse brain: comparison of acetylcholine, nicotine and $\alpha$-bungarotoxin," Mol. Pharmacol., 30:427–436; 1986.

Marrain, Russell, Todd, Biochem. J, 45:533, 1949.

Martin, Panickar, King, Deyrup, Hunter, and Meyer, "Cytoprotective actions of 2,4-dimethoxybenzylidene anabaseine in differentiated PC12 cells and septal cholinergic cells, Drug Develop. Res. 31:127–134; 1994.

Martin, Panickar, King, Deyrup, Hunter, Meyer, "Cytoprotective actions of 2,4-dimethoxybenzylidene anabaseine in differentiated PC12 cells and septol cholinergic cells," Drug Dev. Res., 31:127–134, 1994.

Meyer, Arendash, Judkins, Ying, Wade, and Kem, "Effects of nucleus basalis lesions on the muscarinic and nicotinic modulation of acetylcholine release in the rat cerebral cortex," J. Neurochem., 49:1758–1762, 1987.

Meyer, de Fiebre, Hunter, Simpkins and de Fiebre, "Effects of anabaseine related analogs on rat brain nicotinic receptor binding and on avoidance behavior," Drug Dev. Res., 31:135–141, 1994.

Meyer, de Fiebre, Hunter, Simpkins, Frauworth and de Fiebre, "Effects of anabaseine-related analogs on rat brain nicotinic receptor binding and on avoidance behavior," Drug Dev. Res., 31:135–141, 1994.

Meyer, Meyers and King, "The selective alpha7 nicotinic receptor agonist DMXB protects against neocortical neuron loss after nucleus basalis lesions," Brain Res., IN PRESS.

Meyer, Tay, Papke, Meyers, Huang and de Fiebre, "DMXB improves passive avoidance and Morris water task performances in nucleus basalis lesioned rats in a mecamylamine-sensitive manner," Brain Res., IN PRESS.

Miner and Collins, 1989.

Morris, "Spatial localization does not require the presence of local cues," Learn. Motiv., 12:239–260, 1981.

Newhouse, Sunderland, Tarlot, Blumhardt, Weingartner, Mellow and Murphey, "Intravenous nicotine in Alzheimer's disease: a pilot study," Psychopharmacology, 95:171–175, 1988.

Pabreza, Dhawan and Kellar, "[$^3$H]Cytisine binding to nicotinic cholinergic receptors in brain," Mol. Pharmacol., 39:9–12, 1990.

Page, Everitt, Robbins, Marston, and Wilkinson, "Dissociable effects on spatial maze and passive avoidance acquisition and retention following AMPA and ibotenic acid induced excitotoxic lesions of the basal forebrain in rats: differential dependence on cholinergic neuronal loss," Neuroscience, 43:457–472, 1991.

Papke, "The kinetic properties of neuronal nicotinic receptors: Genetic basis of functional diversity," Prog. Neurobiol., 41:509–531, 1993. Papke R. L., Bencherif M., Lippiello P., Neurosci. Lett., (In Press).

Papke, "The kinetic properties of neuronal nicotinic receptors: genetic basis of functional diversity," Prog Neurobiol., 41:509–531, 1993.

Papke, Bencherif and Lippiello, "An evaluation of neuronal nicotinic acetylcholine receptor activation by quaternary nitrogen compounds indicates that choline in selective for the alpha7 subtype," Neurosci, Lett 213:201–204, 1996.

Paxinos and Watson, "The Rat Brain in Stereotaxic Coordinates," Academic Press, Orlando, Florida, 1986.

Paylo and Rudy, "Cholinergic receptor blockade can impair the rat's performance on both the place learning and cued versions of the Morris water task: the role of age and pool wall brightness," Behav. Brain. Res., 36:79–90, 1990.

Pearl and Darling, J. Org. Chem., 22:1266, 1957.

Pomerleau and Pomerleau, "Introduction in Pomerleau and Pomerleau (eds); Nicotine Replacement: A Critical Evaluation, New York, Alan R. Liss, pp.1–9, 1988.

Prehn, Binctokas. Marcucilli, Krajewski, Reed, Miller, Proc. Nail. Acad. Sci USA 91:12599–12603, 1994.

Pugh and Berg, "Neuronal acetylcholine receptors that bind α-bungarotoxin mediate neurite retraction in calcium-dependent manner," J. Neurosci., 14:889–896, 1994.

Raw, Jarvis, Feyerabend, Russell, "Comparison of nicotine chewing gum and psychological treatments for dependent smokers," Br. Med. J, 281:481–482, 1980.

Rowell and Li, "Dose-response relationship for nicotine-induced up-regulation of rat brain nicotinic receptors," J Neurochem., 68:1982–1989, 1997.

Rukenstein, Rydel and Greene, "Multiple agents rescue PC12 cells from serum free cell death by translation and transcription independent mechanisms," J. Neurosci., 11:2552–2563, 1991.

Sahakian, Jones, Levy, Gray and Warburton, "The effects of nicotine on attention, information processing, and short-term memory in patients with dementia of the Alzheimer type," Brit. J. Psychiat., 154:797–805, 1989.

Seguela, Wadiche, Dineley-Miller, Dani and Patrick, "Molecular cloning, functional properties and distribution of rat brain α7: a nicotinic action channel highly permeable to calcium," J Neurosci., 13:595–604, 1993.

Seguela, Wadiche, Dineley-Miller, Dani, Patrick, "Molecular cloning, functional properties and distribution of rat brain α7: A nicotinic $Ca^{4+}$ ion channel highly permeable to calcium," J. Neurosci., 13:596–604, 1993.

Shimohama, Day, Greenwald, Shafron, Simpkins, Meyer, "Alpha7 nicotinic receptor activation protects against NMDA-induced toxicity in vitro and focal ischernia induced neurotoxicity," Brain Res., in press.

Steinbach and Ifune, "How many kinds of nicotinic acetylcholine receptors are there?" Trends Neurosci, 12:3–6, 1989.

Treinin and Chalfie, "A mutated acetylcholine receptor subunit causes neuronal degeneration in C. elegans," Neuron, 14:871–877, 1995.

U.S. Pat. No. 5,602,257

Vijayaraghavan, Pugh, Zhang, Rathouz, Berg, "Nicotinic receptors that bind α-bungarotoxin on neurons raise intracellular free $Ca^{2+}$," Neuron, 8:353–362, 1992.

Vorlander, Chem. Ber., 39:808, 1906.

Wahlestedt, Golanov, Yamamoto, Yee, Ericson, Yoo, Inturrisi, Reis, "Antisense oligodeoxynucleotides to NMDA-R1 receptor channel protect cortical neurons from excitotoxicity and reduce focal ischoemic infarctions," Nature, 363:260–263, 1993.

Warburton, "Psychopharmacological aspects of nicotine," In: Nicotine Psychopharmacology, Molecular, Cellular and Behavioral Aspects, Wonnacott, et al., eds., pp 77–111, Oxford University Press, New York, 1990.

Woodruf-Pak, Li and Kem, "A nicotinic agonist (GTS-21), eyeblink classical conditioning and nicotinic receptor binding in rabbit brain," Brain Res.

Wright, Zhong, Zheng, Larrick, "Nicotine inhibition of apoptosis suggests a role in tumor promotion," FASEB J, 7:1045, 1993.

Yu, Zhang, Eisele, Benrand, Changeux and Weight, "Ethanol inhibition of nicotinic acetylcholine type alpha7 receptors involves the amino-terminal domain of the receptor," Mol. Pharmacol., 50:1010–1016, 1996.

Zoltewicz, Prokai-Tatrai, Bloom, Kem, "Long range transmission of polar effects in cholinergic 3-arylidene anabaseines. Conformations calculated by molecular modeling," Heterocyclics, 35:171–179, 1993.

What is claimed is:

1. A composition of matter comprising a compound of the formula:

or a salt thereof, wherein $R^1$, $R^6$, and $R^7$ are hydrogen or $C_1$–$C_4$ alkyl; and $R^2$ is =CHCH=CHX, wherein X is wherein $R^3$, $R^4$, and $R^5$ are selected from the group consisting of hydrogen, $C_1$–$C_4$ alkyl optionally substituted with NN-dialkylamino having 1 to 4 carbons in each of the alkyls, $C_1$–$C_6$ alkoxy optionally substituted with N,N-dialkylamino having 1 to 4 carbons in each of the alkyls, carboalkoxy having 1 to 4 carbons in the alkoxy, amino, amino having 1 to 4 carbons in the acyl, cyano, N,N-dialkylamino having 1 to 4 carbons in each of the alkyls, halo, hydroxyl, and nitro.

2. The composition according to claim 1, wherein $R^2$ is attached to the 3-position of the tetrahydropyridine ring.

3. The composition according to claim 2, wherein $R^3$, which is attached to the 4- or the 2-position of the phenyl ring, is selected from the group consisting of amino, hydroxyl, chloro, cyano, dimethylamino, methyl, methoxy, acetylamino, acetoxy, and nitro.

4. The composition according to claim 3, wherein $R^3$ is hydroxyl.

5. The composition according to claim 3, wherein $R^3$ is acetylamino.

6. The composition according to claim 3, wherein $R^3$ is acetoxy.

7. The composition according to claim 3, wherein $R^3$ is methoxy.

8. The composition according to claim 7, wherein $R^1$ and $R^4$ are hydrogen, $R^3$ is attached to the 2-position of the phenyl ring, and $R^5$, which is attached to the 4-position of the phenyl ring, is methoxy or hydroxy.

9. The composition according to claim 4, claim 5, claim 6, or claim 7, wherein $R^1$, $R^4$, and $R^5$ are hydrogen.

10. A composition of matter comprising a cinnamylidene-anabaseine.

11. The composition according to claim 10, wherein the cinnamylidene-anabaseine is selected from the group consisting of 3-(4-acetylaminocinnamylidene) anabaseine, 3-(4-hydroxycinnamylidene) anabaseine, 3-(4-methoxycinnamylidene) anabaseine, 3-(4-hydroxy-2-methoxycinnamylidene)anabaseine, 3-(2,4-dimethoxycinnamylidene) anabaseine, and 3-(4-acetoxycinnamylidene) anabaseine.

12. A composition of matter comprising 3-(4-isopropoxybenzylidene) anabaseine.

13. A method of moderating or preventing tobacco-withdrawal effects in a mammal in need thereof, comprising administering to an animal in need thereof a therapeutically effective amount of a compound of the formula:

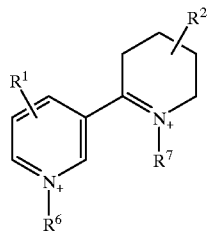

or a pharmaceutically acceptable salt thereof, wherein $R^1$, $R^6$, and $R^7$ are hydrogen or $C_1$–$C_4$ alkyl; and $R^2$ is =CHX, =CCH$_3$X, or =CHCH=CHX, wherein X is

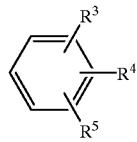

wherein $R^3$, $R^4$, and $R^5$ are selected from the group consisting of hydrogen, $C_1$–$C_4$ alkyl optionally substituted with N,N-dialkylamino having 1 to 4 carbons in each of the alkyls, $C_1$–$C_6$ alkoxy optionally substituted with N,N-dialkylamino having 1 to 4 carbons in each of the alkyls, carboalkoxy having 1 to 4 carbons in the alkoxy, amino, amino having 1 to 4 carbons in the acyl, cyano, N,N-dialkylamino having 1 to 4 carbons in each of the alkyls, halo, hydroxyl, and nitro.

14. The method according to claim 13, wherein $R^2$ is =CH—X or =CCH$_3$X.

15. The method according to claim 14, wherein $R^2$ is attached to the 3-position of the tetrahydropyridine ring.

16. The method according to claim 15, wherein $R^3$, which is attached to the 4-position of the phenyl ring, is selected from the group consisting of amino, hydroxyl, chloro, cyano, dimethylamino, methyl, methoxy, isopropoxy, and nitro.

17. The method according to claim 16, wherein $R^3$ is hydroxyl.

18. The method according to claim 16, wherein $R^3$ is methoxy or isopropoxy.

19. The method according to claim 16, wherein $R^3$ is amino.

20. The method according to claim 15, wherein $R^1$ is hydrogen, $R^3$ is methoxy, $R^4$ is hydroxyl or methoxy, and $R^5$ is hydrogen.

21. The method according to claim 20, wherein $R^3$ is attached to the 4-position of the phenyl ring and $R^4$ is attached to the 2-position of the phenyl ring.

22. The method according to claim 20, wherein $R^3$ is attached to the 2-position of the phenyl ring and $R^4$ is attached to the 4-position of the phenyl ring.

23. The method according to claim 15, wherein $R^1$ is hydrogen, $R^3$, $R^4$ and $R^5$ are all methoxy.

24. The method according to claim 15, wherein $R^3$ is 4-dimethylamino, and $R^4$ and $R^5$ are both hydrogen.

25. The method according to claim 13, wherein $R^2$ is =CHCH=CHX.

26. The method according to claim 25, wherein $R^2$ is attached to the 3-position of the tetrahydropyridine ring.

27. The method according to claim 26, wherein $R^3$, which is attached to the 4- or the 2-position of the phenyl ring, is selected from the group consisting of amino, hydroxyl, chloro, cyano, dimethylamino, methyl, methoxy, acetylamino, acetoxy, and nitro.

28. The method according to claim 27, wherein $R^3$ is hydroxyl.

29. The method according to claim 27, wherein $R^3$ is acetylamino.

30. The method according to claim 27, wherein $R^3$ is acetoxy.

31. The method according to claim 27, wherein $R^3$ is methoxy.

32. The method according to claim 31, wherein $R^1$ and $R^4$ are hydrogen, $R^3$ is attached to the 2-position of the phenyl ring, and $R^5$, which is attached to the 4-position of the phenyl ring, is methoxy or hydroxy.

33. The method according to claim 28, claim 29, claim 30, or claim 31, wherein $R^1$, $R^4$, and $R^5$ are hydrogen.

34. The method according to claim 13, wherein the animal is human.

35. A method of treating tobacco-withdrawal symptoms comprising administering to an animal in need thereof a therapeutically effective amount of a benzylidene-anabaseine or a cinnamylidene-anabaseine capable of selectively activating alpha7 receptors, or a pharmaceutically acceptable salt thereof.

36. The method of claim 35, wherein the benzylidene-anabaseine is selected from the group consisting of 3-(2,4-dimethoxybenzylidene) anabaseine, 3-(4-hydroxybenzylidene) anabaseine, 3-(4-methoxybenzylidene) anabaseine, 3-(4-aminobenzylidene) anabaseine, 3-(4-hydroxy-2-methoxybenzylidene) anabaseine, 3-(2-hydroxy-4-methoxybenzylidene) anabaseine, 3-(4-isopropoxybenzylidene) anabaseine, and (7'-methyl-3-(2,4dimethoxybenzylidene)) anabaseine.

37. The method of claim 35, wherein the cinnamylidene-anabaseine is selected from the group consisting of 3-(4-acetylaminocinnamylidene) anabaseine, 3-(4-hydroxycinnamylidene) anabaseine, 3-(4-methoxycinnamylidene) anabaseine, 3-(4-hydroxy-2-methoxycinnamylidene) anabaseine, 3-(2,4-dimethoxycinnamylidene) anabaseine, and 3-(4-acetoxycinnamylidene) anabaseine.

38. A method of stimulating brain alpha7 receptors antagonized by ethanol in a mammal, comprising administering to an animal in need thereof a therapeutically effective amount of a compound of the formula:

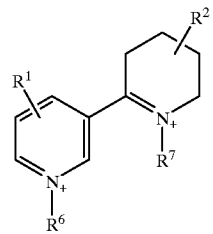

or a pharmaceutically acceptable salt thereof, wherein $R^1$, $R^6$, and $R^7$ are hydrogen or $C_1$–$C_4$ alkyl; and $R^2$ is =CHX, =CCH$_3$X, or =CHCH=CHX, wherein X is

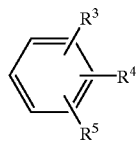

wherein R³, R⁴, and R⁵ are selected from the group consisting of hydrogen, $C_1$–$C_4$ alkyl optionally substituted with N,N-dialkylamino having 1 to 4 carbons in each of the alkyls, $C_1$–$C_6$ alkoxy optionally substituted with N,N-dialkylamino having 1 to 4 carbons in each of the alkyls, carboalkoxy having 1 to 4 carbons in the alkoxy, amino, amino having 1 to 4 carbons in the acyl, cyano, N,N-dialkylamino having 1 to 4 carbons in each of the alkyls, halo, hydroxyl, and nitro.

39. The method according to claim 38, wherein R² is =CH—X or =CCH₃X.

40. The method according to claim 39, wherein R² is attached to the 3-position of the tetrahydropyridine ring.

41. The method according to claim 40, wherein R³, which is attached to the 4-position of the phenyl ring, is selected from the group consisting of amino, hydroxyl, chloro, cyano, dimethylamino, methyl, methoxy, isopropoxy, and nitro.

42. The method according to claim 41, wherein R³ is hydroxyl.

43. The method according to claim 41, wherein R³ is methoxy or isopropoxy.

44. The method according to claim 41, wherein R³ is amino.

45. The method according to claim 40, wherein R¹ is hydrogen, R³ is methoxy, R⁴ is hydroxyl or methoxy, and R⁵ is hydrogen.

46. The method according to claim 45, wherein R³ is attached to the 4-position of the phenyl ring and R⁴ is attached to the 2-position of the phenyl ring.

47. The method according to claim 45, wherein R³ is attached to the 2-position of the phenyl ring and R⁴ is attached to the 4-position of the phenyl ring.

48. The method according to claim 40, wherein R¹ is hydrogen, R³, R⁴ and R⁵ are all methoxy.

49. The method according to claim 40, wherein R³ is 4-dimethylamino, and R⁴ and R⁵ are both hydrogen.

50. The method according to claim 38, wherein R² is =CHCH=CHX.

51. The method according to claim 50, wherein R² is attached to the 3-position of the tetrahydropyridine ring.

52. The method according to claim 51, wherein R³, which is attached to the 4- or the 2-position of the phenyl ring, is selected from the group consisting of amino, hydroxyl, chloro, cyano, dimethylamino, methyl, methoxy, acetylamino, acetoxy, and nitro.

53. The method according to claim 52, wherein R³ is hydroxyl.

54. The method according to claim 52, wherein R³ is acetylamino.

55. The method according to claim 52, wherein R³ is acetoxy.

56. The method according to claim 52, wherein R³ is methoxy.

57. The method according to claim 56, wherein R¹ and R⁴ are hydrogen, R³ is attached to the 2-position of the phenyl ring, and R⁵, which is attached to the 4-position of the phenyl ring, is methoxy or hydroxy.

58. The method according to claim 53, claim 54, claim 55, or claim 56, wherein R¹, R⁴, and R⁵ are hydrogen.

59. The method according to claim 38, wherein the animal is human.

60. A method of stimulating brain alpha7 receptors antagonized by ethanol comprising administering to an animal in need thereof a therapeutically effective amount of a benzylidene-anabaseine or a cinnamylidene-anabaseine capable of selectively activating alpha7 receptors, or a pharmaceutically acceptable salt thereof.

61. The method of claim 60, wherein the benzylidene anabaseine is selected from the group consisting of 3-(2,4-dimethoxybenzylidene) anabaseine, 3-(4-hydroxybenzylidene) anabaseine, 3-(4-methoxybenzylidene) anabaseine, 3-(4-aminobenzylidene) anabaseine, 3-(4-hydroxy-2-methoxybenzylidene) anabaseine, 3-(2-hydroxy-4-methoxybenzylidene) anabaseine, 3-(4-isopropoxybenzylidene) anabaseine, and (7'-methyl-3-(2,4-dimethoxybenzylidene)) anabaseine.

62. The method of claim 60, wherein the cinnamylidene-anabaseine is selected from the group consisting of 3-(4-acetylaminocinnamylidene) anabaseine, 3-(4-hydroxycinnamylidene) anabaseine, 3-(4-methoxycinnamylidene) anabaseine, 3-(4-hydroxy-2-methoxycinnamylidene)anabaseine, 3-(2,4-dimethoxycinnamylidene)anabaseine, and 3-(4-acetoxycinnamylidene) anabaseine.

63. A method of protecting against cell loss induced by ischemia in a mammal, comprising administering to an animal in need thereof a therapeutically effective amount of a compound of the formula:

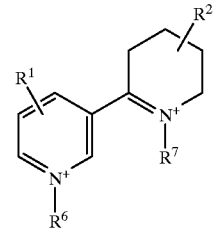

or a pharmaceutically acceptable salt thereof, wherein R¹, R⁶, and R⁷ are hydrogen or $C_1$–$C_4$ alkyl; and R² is =CHX, =CCH₃X, or =CHCH=CHX, wherein X is

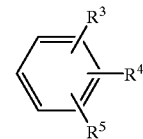

wherein R³, R⁴, and R⁵ are selected from the group consisting of hydrogen, $C_1$–$C_4$ alkyl optionally substituted with N,N-dialkylamino having 1 to 4 carbons in each of the alkyls, $C_1$–$C_6$ alkoxy optionally substituted with N,N-dialkylamino having 1 to 4 carbons in each of the alkyls, carboalkoxy having 1 to 4 carbons in the alkoxy, amino, amino having I to 4 carbons in the acyl, cyano, N,N-dialkylamino having 1 to 4 carbons in each of the alkyls, halo, hydroxyl, and nitro.

64. The method according to claim 63, wherein R² is =CH—X or =CCH₃X.

65. The method according to claim 64, wherein R² is attached to the 3-position of the tetrahydropyridine ring.

66. The method according to claim 65, wherein R³, which is attached to the 4-position of the phenyl ring, is selected from the group consisting of amino, hydroxyl, chloro, cyano, dimethylamino, methyl, methoxy, isopropoxy, and nitro.

67. The method according to claim 66, wherein $R^3$ is hydroxyl.

68. The method according to claim 66, wherein $R^3$ is methoxy or isoproxy.

69. The method according to claim 66, wherein $R^3$ is amino.

70. The method according to claim 65, wherein $R^1$ is hydrogen, $R^3$ is methoxy, $R^4$ is hydroxyl or methoxy, and $R^5$ is hydrogen.

71. The method according to claim 70, wherein $R^3$ is attached to the 4-position of the phenyl ring and $R^4$ is attached to the 2-position of the phenyl ring.

72. The method according to claim 70, wherein $R^3$ is attached to the 2-position of the phenyl ring and $R^4$ is attached to the 4-position of the phenyl ring.

73. The method according to claim 65, wherein $R^1$ is hydrogen, $R^3$, $R^4$ and $R^5$ are all methoxy.

74. The method according to claim 65, wherein $R^3$ is 4-dimethylamino, and $R^4$ and $R^5$ are both hydrogen.

75. The method according to claim 63, wherein $R^2$ is =CHCH=CHX.

76. The method according to claim 75, wherein $R^2$ is attached to the 3-position of the tetrahydropyridine ring.

77. The method according to claim 76, wherein $R^3$, which is attached to the 4- or the 2-position of the phenyl ring, is selected from the group consisting of amino, hydroxyl, chloro, cyano, dimethylamino, methyl, methoxy, acetylamino, acetoxy, and nitro.

78. The method according to claim 77, wherein $R^3$ is hydroxyl.

79. The method according to claim 77, wherein $R^3$ is acetylamino.

80. The method according to claim 77, wherein $R^3$ is acetoxy.

81. The method according to claim 77, wherein $R^3$ is methoxy.

82. The method according to claim 81, wherein $R^1$ and $R^4$ are hydrogen, $R^3$ is attached to the 2-position of the phenyl ring, and $R^5$, which is attached to the 4-position of the phenyl ring, is methoxy or hydroxy.

83. The method according to claim 78, claim 79, claim 80, or claim 81, wherein $R^1$, $R^4$, and $R^5$ are hydrogen.

84. The method according to claim 63, wherein the animal is human.

85. The method of claim 63, wherein the cell loss is from stroke.

86. The method of claim 63, wherein the cell loss is from glutamate-induced excitotoxicity.

87. A method of protecting against cell loss induced by ischemia comprising administering to an animal in need thereof a therapeutically effective amount of a benzylidene-anabaseine or a cinnamylidene-anabaseine capable of selectively activating alpha7 receptors, or a pharmaceutically acceptable salt thereof.

88. The method of claim 87, wherein the benzylidene-anabaseine is selected from the group consisting of 3-(2,4-dimethoxybenzylidene) anabaseine, 3-(4-hydroxybenzylidene) anabaseine, 3-(4-methoxybenzylidene) anabaseine, 3-(4-aminobenzylidene) anabaseine, 3-(4-hydroxy-2-methoxybenzylidene) anabaseine, 3-(2-hydroxy-4-methoxybenzylidene) anabaseine, 3-(4-isopropoxybenzylidene) anabaseine, and (7'-methyl-3-(2,4-dimethoxybenzylidene)) anabaseine.

89. The method of claim 87, wherein the cinnamylidene-anabaseine is selected from the group consisting of 3-(4-acetylaminocinnamylidene) anabaseine, 3-(4-hydroxycinnamylidene) anabaseine, 3-(4-methoxycinnamylidene) anabaseine, 3-(4-hydroxy-2-methoxycinnamylidene)anabaseine, 3-(2,4-dimethoxycinnamylidene)anabaseine, and 3-(4-acetoxycinnamylidene) anabaseine.

90. A method of prophylaxis against cell loss from focal ischemic insult, comprising administering to a mammal in need thereof an amount of an alpha7 nicotinic agonist selected from the group consisting of a benzylidene-anabaseine and a cinnamylidene-anabaseine before occurrence of ischemia in an amount effective to protect against the cell loss.

91. The method according to claim 90, wherein the benzylidene-anabaseine is selected from the group consisting of 3-(2,4-dimethoxybenzylidene) anabaseine, 3-(4-hydroxybenzylidene) anabaseine, 3-(4-methoxybenzylidene) anabaseine, 3-(4-aminobenzylidene) anabaseine, 3-(4-hydroxy-2-methoxybenzylidene) anabaseine, 3-(2-hydroxy-4-methoxybenzylidene) anabaseine, 3-(4-isopropoxybenzylidene) anabaseine, and (7'-methyl-3-(2,4-dimethoxybenzylidene)) anabaseine.

92. The method according to claim 90, wherein the cinnamylidene-anabaseine is selected from the group consisting of 3-(4-acetylaminocinnamylidene) anabaseine, 3-(4-hydroxycinnamylidene) anabaseine, 3-(4-methoxycinnamylidene) anabaseine, 3-(4-hydroxy-2-methoxycinnamylidene)anabaseine, 3-(2,4-dimethoxycinnamylidene) anabaseine, and 3-(4-acetoxycinnamylidene) anabaseine.

93. A method of treating age related learning or memory impairment comprising administering to an animal in need thereof a therapeutically effective amount of a cinnamylidene-anabaseine.

94. The method according to claim 93, wherein the cinnamylidene-anabaseine is selected from the group consisting of 3-(4-acetylaminocinnamylidene) anabaseine, 3-(4-hydroxycinnamylidene) anabaseine, 3-(4-methoxycinnamylidene) anabaseine, 3-(4-hydroxy-2-methoxycinnamylidene)anabaseine, 3-(2,4-dimethoxycinnamylidene) anabaseine, and 3-(4-acetoxycinnamylidene) anabaseine.

* * * * *

UNITED STATES PATENT AND TRADEMARK OFFICE
CERTIFICATE OF CORRECTION

PATENT NO. : 5,977,144      Page 1 of 1
DATED : November 2, 1999
INVENTOR(S) : Edwin M. Meyer; William R. Kem; Frans van Haaren; John A. Zoltewicz; Christopher M. De Fiebre; Roger Papke; Arthur Day It is certified that error appears in the above-identified patent and that said Letters Patent is hereby corrected as shown below:

Title page,
Inventor(s), -- Edwin M. Meyer; William R. Kem; Frans van Haaren; John A. Zoltewicz, all of Gainesville, Fla., Christopher M. de Fiebre, Forth Worth, Tex., Roger Papke; Arthur L. Day, both of Gainesville, Fla. --

Signed and Sealed this

Fifth Day of March, 2002

Attest:

*Attesting Officer*

JAMES E. ROGAN
*Director of the United States Patent and Trademark Office*